(12) United States Patent
Josephson et al.

(10) Patent No.: US 8,535,949 B2
(45) Date of Patent: Sep. 17, 2013

(54) WATER RELAXATION-BASED SENSORS

(75) Inventors: Lee Josephson, Reading, MA (US); Yi Sun, Malden, MA (US); Ralph Weissleder, Peabody, MA (US)

(73) Assignee: The General Hospital Corporation, Boston, MA (US)

( * ) Notice: Subject to any disclaimer, the term of this patent is extended or adjusted under 35 U.S.C. 154(b) by 335 days.

(21) Appl. No.: 12/612,126

(22) Filed: Nov. 4, 2009

(65) Prior Publication Data

US 2010/0120174 A1 May 13, 2010

Related U.S. Application Data

(62) Division of application No. 11/431,247, filed on May 9, 2006, now abandoned.

(60) Provisional application No. 60/679,437, filed on May 9, 2005.

(51) Int. Cl.
*G01N 33/553* (2006.01)

(52) U.S. Cl.
USPC ........... 436/526; 436/518; 436/524; 436/525; 977/840; 977/953; 977/960; 435/7.1; 435/283.1; 435/287.2; 600/300; 600/309; 600/316

(58) Field of Classification Search
USPC ......... 436/518, 524, 525, 526, 536; 977/840, 977/953, 960; 435/7.1, 283.1, 287.2; 600/300, 600/309, 316
See application file for complete search history.

(56) References Cited

U.S. PATENT DOCUMENTS

| | | | |
|---|---|---|---|
| 4,875,486 | A | 10/1989 | Rapoport et al. |
| 5,136,095 | A | 8/1992 | Tarnowski et al. |
| 5,153,166 | A | 10/1992 | Jain et al. |
| 5,164,297 | A | 11/1992 | Josephson et al. |
| 5,254,460 | A | 10/1993 | Josephson et al. |
| 5,445,971 | A | 8/1995 | Rohr |
| 6,013,188 | A | 1/2000 | Terstappen et al. |
| 6,097,188 | A | 8/2000 | Sweedler et al. |
| 6,194,900 | B1 | 2/2001 | Freeman et al. |
| 6,256,522 | B1 | 7/2001 | Schultz |
| 6,297,062 | B1 | 10/2001 | Gombinski |
| 6,342,396 | B1 | 1/2002 | Perrin et al. |
| 6,361,944 | B1 | 3/2002 | Mirkin et al. |
| 6,500,343 | B2 | 12/2002 | Siddiqi |
| 6,509,059 | B2 | 1/2003 | Yang et al. |
| 6,630,355 | B1 | 10/2003 | Pivarnik et al. |

(Continued)

FOREIGN PATENT DOCUMENTS

| | | |
|---|---|---|
| WO | 9006045 A2 | 6/1990 |
| WO | 9117428 | 11/1991 |

(Continued)

OTHER PUBLICATIONS

Lambert et al., Intradermal vaccine delivery: Will new delivery systems transform vaccine administration?, 2008, Vaccine, vol. 26, pp. 3197-3208.*

(Continued)

*Primary Examiner* — Melanie Y Brown
(74) *Attorney, Agent, or Firm* — Fish & Richardson P.C.

(57) ABSTRACT

This invention relates to magnetic resonance-based sensors and related methods.

13 Claims, 15 Drawing Sheets

(56) References Cited

U.S. PATENT DOCUMENTS

| | | | |
|---|---|---|---|
| 6,751,491 B2 | 6/2004 | Lew et al. | |
| 6,767,635 B1 | 7/2004 | Bahr et al. | |
| 7,018,849 B2 | 3/2006 | Piasio et al. | |
| 2003/0092029 A1 | 5/2003 | Josephson et al. | |
| 2003/0174384 A1 | 9/2003 | Halas et al. | |
| 2003/0222648 A1 | 12/2003 | Fan | |
| 2007/0281368 A1* | 12/2007 | Hsieh et al. | 436/501 |

FOREIGN PATENT DOCUMENTS

| | | |
|---|---|---|
| WO | 9740181 A1 | 10/1997 |
| WO | 9804740 A1 | 2/1998 |
| WO | 0100876 A1 | 1/2001 |
| WO | 0111360 A2 | 2/2001 |
| WO | 0119405 A2 | 3/2001 |
| WO | 02098364 | 12/2002 |
| WO | 2005061724 | 7/2005 |
| WO | 2005099419 A2 | 10/2005 |

OTHER PUBLICATIONS

Atanasijevic et al., "Calcium-sensitive MRI contrast agents based on superparamagnetic iron oxide nanoparticles and calmodulin", PNAS 130(40)pp. 14707-14712, 2006.
Costanzo et al.,"Protein-ligand mediated aggregation of nanoparticles: a study of synthesis and assembly mechanism", Chem Mater 16:1775-1785, 2004.
Fry et al., "A new approach to template purification for sequencing applications using paramagnetic particles", 13 (1), pp. 124-131, 1992.
Josephson et al., "High-efficiency intracellular magnetic labeling with novel superparamagnetic-TAT peptide conjugates", Bioconjugate Chem. 10(2) pp. 186-191, Jan. 4, 1999.
Josephson et al.,"Magnetic nanosensors for the detection of oligonucleotide sequences", Angew Chem 40 (17):3204-3206, 2001.
Kotitz et al., "Determination of the binding reaction between avidin and biotin by relaxation measurements of magnetic nanoparticles", Journal of Magnetism and Magnetic Materials 194:62-68, 1999.
Lee et al., "Microelectromagnets for the control of magnetic nanoparticles"; Appl Phys letters 79:3308-3310, 2001.
Lewin et al., "TAT peptide-derivatised magneitc nanoparticles allow in vivo tracking and revcovery of progenitor cells", vol. 18, pp. 410-414, 2000.
Magin et al., "Miniature magnetic resonance machines", IEEE Spectrum, vol. 34(10):51-61, 1997.
Massin et al., "Planar micricoil-based microfluidic NMR probes" J. Magnetic Resonance vol. 164, pp. 242-255, 2003.
Massin et al., "Planar microcoil-based magnetic resonance imaging of cells", Transducers, Solid-state Sensors, Actuators and Microsystems 12th Int'l conference 2(9):967-970, 2003.
Niemeyer et al., "Self-assembly of DNA-strepavidiv nanostructrues and their use ias reagents in Immuno-PCR", Nucleic Acid Research 27(23):4553-4561, 1999.
Peck et al., "RF microcoils patterned using microlithographic techniques for use as microsensors in NMR", Engineering in Medicine and Biologu Scoiety, Proceedings of the 15th annual international conference of the IEEE, Oct. 28-31, 1993; pp. 174-175, 1993.
Perez et al., "DNA-based magnetic nanoparticle assembly acts as a magnetic relaxation nanoswitch allowing of DNA-cleaving agents", J. Am. Chem. Soc. 124(12):2856-2857, Dec. 14, 2001.
Perez et al., "Viral—induced self assembly of magnetic nanoparticles allows the detection of viral particles in biological media", J. Am. Chem. Soc. 125:10192-10193, 2003.
Shapiro et al., "Dynamic imaging eith MRI contrast agents: quantitative considerations", Magnetic Resonance Imaging 24:449-462, 2006.
Sillerrud et al, "1H NMR detection of superparamagnetic nanoparticles at 1 T using a microcoil and novel tuning circuit", JMR 181:181-190, 2006.
Weissleder et al., "Cell-specific targeting of nanoparticles by multivalent attachment of small molecules", Nature Biotechnology, 23(11):1418-1423, 2005.
Wu et al., "1H-NMR spectroscopy on the nanoliter scale for static and on-line measurements", Anal. Chem. 66:3849-3857, 1994.
Sun et al., "Continuous analyte sensing with magnetic nanoswitches", Small, Wiley—VCH Verlag GmbH & Co., KGAA, Germany, vol. 2, No. 10, Oct. 1, 2006, pp. 1144-1147.
Search Report from corresponding European Application No. 11172503.2-2209, issued Oct. 11, 2011, 5 pages.
Gijs, "Magnetic bead handling on-chip: new opportunities for analytical applications," Microfluid Nanofluid, vol. 1, pp. 22-40, 2004, XP002418117.
Perez et al, "Magnetic relaxation switches capable of sending molecular interactions," Nature Biotechnology, vol. 20, No. 8, pp. 816-820, 2002.
Perez et al., "Use of magnetic nanoparticles as nanosensors to probe for molecular interactions," Chembiochem, Wiley-Vch Verlag., vol. 5, No. 3, pp. 261-264, 2004.
Rogers et al., "Use of uspio-induced magnetic susceptibility artifacts to identify sentinel lymph nodes and lymphatic drainage patterns—1—Dependence of artifact size with subcutaneous Combidex® dose in rats," Magnetic Resonance Imaging, vol. 16, No. 8, pp. 917-923, 1998.
Taketomi-Takahashi et al., "Magnetite ingested as a nutritional supplement: Unexpected source of MRI susceptibility artifact," American Journal of Roentgenology, vol. 188, pp. 1026-1027, 2007.

* cited by examiner

WATER RELAXATION-BASED SENSORS

CROSS REFERENCE TO RELATED APPLICATIONS

This application is a divisional application of U.S. application Ser. No. 11/431,247, filed on May 9, 2006, which claims the benefit of priority of U.S. Provisional Application 60/679,437, filed on May 9, 2005. Both of these applications are incorporated herein by reference in their entirety.

STATEMENT REGARDING FEDERALLY SPONSORED RESEARCH

The work described herein was carried out, at least in part, using funds from National Institutes of Health (NIH) Grants R01 EB004626 and EB00662. The government therefore has certain rights in the invention.

TECHNICAL FIELD

This invention relates to magnetic resonance-based sensors and related methods.

BACKGROUND

Magnetic resonance (MR)-based reporting methods, such as magnetic resonance imaging (MRI), offer certain known advantages as non-invasive methods. For example, MRI can be used at tissue depths where optical reporting methods can sometimes be complicated by light scattering and absorption by the tissue, e.g., tissue depths greater than about 250 µm.

One application of nanotechnology in medicine is the development of biocompatible nanomaterials as environmentally sensitive sensors and molecular imaging agents. Preparations of magnetic particles designed for separation and extraction use particles that are amenable to easy manipulation by weak applied magnetic fields. These materials are typically micron sized and have a high magnetic moment per particle. However, nanoparticles do not respond to the weak, magnetic fields of hand held magnets.

SUMMARY

This invention relates generally to magnetic resonance-based sensors (e.g., water relaxation and equilibrium-based sensors) and related methods, and is based, in part, on the discovery that sensors having magnetic nanoparticles encapsulated within a semipermeable enclosure can be used as remote sensors for detecting various analytes in an aqueous, e.g., a water-containing, sample and can be used for the continuous monitoring of changing levels of the analytes.

In its broadest aspects, the invention provides a water relaxation-based sensor for detecting the presence of an analyte in a sample. The sensor includes an enclosure defining an opening for entry of the analyte, e.g., a semipermeable membrane, and confined within said enclosure, a plurality of nanoparticles. The nanoparticles are suspended or suspendable in an aqueous liquid phase, have a magnetic moment, e.g., comprise crystalline iron oxide or other magnetic material, and are covalently or non covalently linked to, or otherwise have immobilized thereon, one or more moieties selected to alter the state of aggregation of the nanoparticles as a function of the presence or concentration of the analyte in the enclosure.

In one aspect, this invention features water relaxation-based sensors for detecting the presence of an analyte (e.g., an exogenous analyte) in a sample. The sensors include: (i) a walled enclosure enveloping a chamber, wherein the wall includes one or more openings (e.g., a single opening or a plurality of openings) for passage of the analyte into and out of the chamber; (ii) a plurality of magnetic nanoparticles located within the chamber, each nanoparticle having at least one moiety that is covalently or noncovalently linked to (immobilized on) the nanoparticle; and optionally, (iii) at least one binding agent located within the chamber, in which the opening can be smaller in size than the nanoparticles and the binding agent and larger in size than the analyte; and the moiety and the analyte can each bind reversibly to the binding agent, when present; or the analyte can bind reversibly to the moiety. In some embodiments, the openings can be larger than the binding agent, as long as the binding agents remain within the chamber when bound to the nanoparticles.

Embodiments can include one or more of the following features.

The nanoparticles can be suspended or be suspendable in an aqueous liquid phase. The nanoparticles can have a magnetic moment generally, or under certain conditions.

The wall can include more than one opening. When the wall contains more than one opening (e.g., a plurality of openings), then at least one of the openings is smaller in size than the nanoparticles and optionally the binding agent, and larger in size than the analyte. In certain embodiments, the wall includes a plurality of openings, in which each of the openings is smaller in size than the nanoparticles and the binding agent, and each of the openings is larger in size than the analyte.

The moiety can be selected to alter the state of aggregation of the nanoparticles as a function of the presence or concentration of the analyte in the enclosure.

In its several alternative embodiments, the sensor may exploit different detection formats. For example, the moiety may be selected to bind to the analyte to produce an aggregate of plural linked nanoparticles as a function of the presence or concentration of the analyte in the enclosure. The sensor may include an aggregate of plural linked nanoparticles, which is disaggregated as a function of the presence or concentration of the analyte in the enclosure. The moiety may be a fragment of an authentic sample of the analyte or a structural mimic thereof, in which case the sensor further includes a multivalent binding agent, which binds to the analyte and the mimic (if used) to produce an aggregate of plural linked nanoparticles. The sensor can further include a multivalent binding agent which binds to the moiety to produce an aggregate. The sensor also can include a binding agent, which binds to the moiety in the presence of the analyte to disassociate an aggregate. In yet another form, the sensor can include a binding agent that binds to the moiety in the presence of the analyte to produce an aggregate. In one embodiment, the sensor further includes a plurality of aggregates confined within the enclosure. In another embodiment, the sensor includes a sample flow path in communication with the interior of the enclosure. Thus, the sample can flow into, or into and out of, the enclosure to permit periodic sampling of the analyte.

In some embodiments, the sensors include features (i), (ii), and (iii) above; the moiety can be, or can include as part of its chemical structure, a molecular fragment of the analyte being detected or a molecular fragment of a derivative, isostere, or mimic of the analyte being detected; and the binding agent can be a protein. When the analyte is absent, the chamber can include one or more nanoparticle aggregates. Each of the nanoparticle aggregates can include one or more nanoparticles and the binding agent. Formation of the nanoparticle aggregate can occur through binding of a moiety on the nanoparticle to the binding agent (e.g., the binding agent can include one or more binding sites that are recognized for binding by the moiety).

When the analyte is present, the chamber can include substantially disaggregated nanoparticles. The analyte, when present, can displace the nanoparticles from the nanoparticle conjugates, thereby providing substantially disaggregated nanoparticles (e.g., the analyte and the moiety can be selected such that the analyte and the nanoparticles can compete for binding with the binding agent, and the analyte, when present, can displace the nanoparticles from the binding agent in the aggregate to provide disaggregated nanoparticles).

In certain embodiments, (a) when the analyte is absent, the chamber can include a nanoparticle aggregate, wherein the nanoparticle aggregate can include nanoparticles bound to the binding agent through the moiety; and (b) when the analyte is present, the nanoparticles are displaced from the binding agent by the analyte, and the chamber comprises substantially disaggregated nanoparticles. In the presence of a water-containing liquid media, the change in nanoparticle aggregation (from nanoparticle aggregates to substantially disaggregated nanoparticles and vice versa, e.g., the difference between (a) and (b) above) alters the proton relaxation of water inside of the chamber, but does not substantially alter the proton relaxation of water outside of the chamber.

In some embodiments, the sensors include features (i) and (ii) above, feature (iii) is absent; and the moiety can be, or can include as part of its chemical structure, a protein. When the analyte is absent, the chamber can include substantially disaggregated nanoparticles. When the analyte is present, the chamber can include one or more nanoparticle aggregates. Each of the nanoparticle aggregates can include one or more nanoparticles and the analyte. Formation of the nanoparticle aggregate can occur through binding of the analyte to the moiety on the nanoparticle (e.g., the moiety can include one or more binding sites that are recognized for binding by the analyte).

In certain embodiments, (a) when the analyte is absent, the chamber comprises substantially disaggregated nanoparticles; and (b) when the analyte is present, the chamber comprises a nanoparticle aggregate, wherein the nanoparticle aggregate comprises nanoparticles bound to the analyte through the moiety. In the presence of a water-containing liquid media, the change in nanoparticle aggregation (from nanoparticle aggregates to substantially disaggregated nanoparticles and vice versa e.g., the difference between (a) and (b) above) alters the proton relaxation of water inside of the chamber, but does not substantially alter the proton relaxation of water outside of the chamber.

In one aspect, this invention features methods of detecting an analyte in an aqueous sample (e.g., monitoring the presence or concentration of an analyte in a sample stream), the methods include: (i) providing a sensor as described herein; (ii) measuring relaxation times (e.g., T2 or T1 relaxation times) of the water inside of the chamber of the sensor in the absence of the analyte or under conditions that mimic the absence of the analyte; (iii) contacting the sensor with the sample (e.g., the nanoparticles can be suspended, or suspendable, in an aqueous liquid phase and can also have a magnetic moment); (iv) measuring relaxation times (e.g., T2 or T1 relaxation times) of the water inside of the chamber of the sensor; and (v) comparing the T2 relaxation times measured in step (ii) and step (iv). A change (e.g., an increase or decrease) in T2 relaxation times measured in step (iv) relative to the T2 relaxation times measured in step (ii) indicates the presence of the analyte.

For example, one can flow a sample stream into the enclosure, allow analyte in the sample to alter the state of aggregation of nanoparticles (e.g., suspended nanoparticles), and measures perturbation of the magnetic resonance relaxivity of water protons disposed adjacent the nanoparticles. These steps can be repeated to obtain a temporal profile of the concentration of the analyte in the stream.

Embodiments can include one or more of the following features.

The nanoparticles can be suspended or be suspendable in an aqueous liquid phase. The nanoparticles can have a magnetic moment.

The wall can include more than one opening. When the wall contains more than one openings (e.g., a plurality of openings), then at least one of the opening is smaller in size than the nanoparticles and the binding agent, and larger in size than the analyte. In certain embodiments, the wall includes a plurality of openings, in which each of the openings is smaller in size than the nanoparticles and the binding agent, and each of the openings is larger in size than the analyte.

The moiety can be selected to alter the state of aggregation of the nanoparticles as a function of the presence or concentration of the analyte in the enclosure. The moiety and the analyte can each bind reversibly to the binding agent, when present; or the analyte can bind reversibly to the moiety. The analyte can be a monovalent or multivalent analyte.

The moiety can be, or can include as part of its structure, a carbohydrate, an antibody, an amino acid, a nucleic acid, an oligonucleotide, a therapeutic agent or a metabolite thereof, a peptide, or a protein. The moiety can be a covalently or noncovalently linked analyte (e.g., the analyte that is being detected, sometimes referred to as a bound analyte or a bound binding protein), a covalently or noncovalently linked analyte derivative, or a covalently or noncovalently linked analyte isostere or mimic (e.g., a derivative, isostere, or mimic of the analyte that is being detected).

In some embodiments, the moiety can be, or can include as part of its structure, a molecular fragment of the analyte being detected or a molecular fragment of a derivative, isostere, or mimic of the analyte being detected.

As used herein and throughout, a moiety that includes "a molecular fragment of the analyte being detected" (or that includes a molecular fragment of a derivative, isostere, or mimic of the analyte being detected) is one in which a portion (e.g., a substantial portion) of the chemical structure of the analyte being detected (or a derivative, isostere, or mimic thereof) is incorporated into the chemical structure of the moiety. In these embodiments, the nanoparticle can have the general formula (A): $(A)_z$-$NP^c$; in which "A" is a molecular fragment of an analyte, A-X, in which X is a hydrogen atom or a functional group that is present in the analyte, but not incorporated into the nanoparticle of formula (A); "$NP^c$" is the nanoparticle core, "-" is a covalent linkage (e.g., a chemical bond or linking functional group) that connects any atom of the fragment to the nanoparticle; and z is 1-50 (e.g., 1-40, 1-30, 1-25, 1-20, 2-20). "A" in the above formula can also be the molecular fragment of a derivative, isostere, or mimic of the analyte being detected.

The moiety can be a protein or a nucleic acid.

The binding agent can be absent. The moiety can be, or include as part of its structure, a protein. In some embodiments, (a) when the analyte is absent, the chamber includes substantially disaggregated nanoparticles; and (b) when the analyte is present, the chamber can include one or more nanoparticle aggregates. Each of the nanoparticle aggregates can include one or more nanoparticles and the analyte. Formation of the nanoparticle aggregate can occur through binding of the analyte to the moiety on the nanoparticle (e.g., the moiety can include one or more binding sites that are recognized for binding by the analyte).

In some embodiments, (a) when the analyte is absent, the chamber comprises substantially disaggregated nanoparticles; and (b) when the analyte is present, the chamber comprises a nanoparticle aggregate, wherein the nanoparticle aggregate comprises nanoparticles bound to the analyte through the moiety.

The binding agent can be present, it can be, for example, a protein or a monoclonal antibody. The moiety can be, or can include as part of its structure, a molecular fragment of the analyte being detected or a molecular fragment of a derivative, isostere, or mimic of the analyte being detected.

In some embodiments, (a) when the analyte is absent, the chamber can include one or more nanoparticle aggregates; and (b) when the analyte is present, the chamber can include substantially disaggregated nanoparticles. Each of the nanoparticle aggregates can include one or more nanoparticles and the binding agent. Formation of the nanoparticle aggregate can occur through binding of a moiety on the nanoparticle to the binding agent (e.g., the binding agent can include one or more binding sites that are recognized for binding by a chemical group that is present as all or part of the chemical structure of the moiety). The analyte, when present, can displace the nanoparticles from the nanoparticle conjugates, thereby providing substantially disaggregated nanoparticles (e.g., the analyte and the nanoparticle substituent can be selected such that the analyte and the nanoparticle moiety can compete for binding with the binding agent, and the analyte, when present, can displace the nanoparticles from the binding agent in the aggregate to provide disaggregated nanoparticles).

In some embodiments, (a) when the analyte is absent, the chamber can include a nanoparticle aggregate, wherein the nanoparticle aggregate can include nanoparticles bound to the binding agent through the moiety; and (b) when the analyte is present, the nanoparticles are displaced from the binding agent by the analyte, and the chamber comprises substantially disaggregated nanoparticles. The change in nanoparticle aggregation between (a) and (b) can alter the proton relaxation of water inside of the chamber, but does not substantially alter the proton relaxation of water outside of the chamber.

The change in nanoparticle aggregation between (a) and (b) can produce a measurable change in the T2 relaxation times of water inside the chamber, and the change in the T2 relaxation times can be measurable using a magnetic resonance imaging or non-imaging method.

The moiety can be linked to the nanoparticle by a functional group such as —NH—, —NHC(O)—, —(O)CNH—, —NHC(O)(CH$_2$)$_n$C(O), —(O)C(CH$_2$)$_n$C(O)NH—, —NHC(O)(CH$_2$)C(O)NH—, —C(O)O—, —OC(O)—, or —SS—, in which n can be 0-20, e.g., 2, 5, 10, or 15. Each of the openings can have a size (pore size) of from about 1 kDa to about 1 μm (e.g., about 1 kDa to about 300,000 kDa; about 1 kDa to about 100,000 kDa; about 1 kDa to about 5 kDa; 1 kDa to about 3 kDa; 1 kDA to about 1 μm).

Each of the nanoparticles can have a particle size or overall size of from about 10 nm to about 500 nm (e.g., about 10 nm to about 60 nm, about 30 nm to about 60 nm). The overall size is the largest dimension of a particle. The nanoparticle aggregate can have an overall size (particle size) of at least about 100 nm. The nanoparticles can be substantially aggregated (e.g., include on or more nanoparticle aggregates) or substantially disaggregated. The analyte can be a carbohydrate (e.g., glucose).

The analyte can be chiral. The chiral analyte can be present together with one or more optically active moieties in the sample. The chiral analyte can be present together with a stereoisomer of the chiral analyte in the sample. The chiral analyte can be present together with the enantiomer of the chiral analyte in the sample. The chiral exogenous analyte can be an amino acid.

The analyte can be a nucleic acid or an oligonucleotide.

The analyte can be a therapeutic agent, which as used herein refers to a bioactive moiety, which when administered to a subject (e.g., a human or animal subject) confers a therapeutic, biological, or pharmacological effect (e.g., treats, controls, ameliorates, prevents, delays the onset of, or reduces the risk of developing one or more diseases, disorders, or conditions or symptoms thereof) on the subject, or a metabolite thereof. The analyte can be, e.g., folic acid.

The analyte can be a peptide or a protein (e.g., influenza hemagglutinin peptide).

The moiety can be, or can include as part of its structure, a chiral moiety. The moiety can be, or can include as part of its structure, an amino acid, a nucleic acid, an oligonucleotide, a therapeutic agent, a metabolite of a therapeutic agent, a peptide, or a protein. The moiety can be, or can include as part of its structure, a carbohydrate (e.g., having the structure:

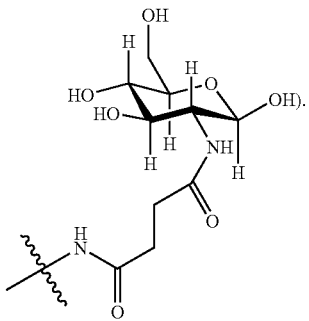

The binding agent can be a protein that includes at least two binding sites or at least four binding sites. The binding agent can be a recombinant protein or be a complex of proteins each with binding sites. The complex of proteins may be assembled by crosslinking. The binding agent can be a protein that binds to a carbohydrate (e.g., glucose). The protein can be conconavalin A. The binding agent can be a monoclonal antibody, a polyclonal antibody, or a oligonucleotide. The binding agent can be, e.g., an antibody to folic acid or an antibody to influenza hemagglutinin peptide. The analyte and the nanoparticle can bind reversibly to the binding agent.

The magnetic nanoparticles each can include a magnetic metal oxide (e.g., a superparamagnetic metal oxide). The metal oxide can be iron oxide. Each of the magnetic nanoparticles can be an amino-derivatized cross-linked iron oxide nanoparticle.

The sensor can be configured to be an implantable sensor. For example, the sensor can be implanted subcutaneously. In certain embodiments, the sensor can be implanted in an extremity of a subject (e.g., a human or animal).

Steps (ii) and (iv) can include measuring T2 relaxation times or T1 relaxation times. An increase in T2 relaxation times measured in step (iv) relative to the T2 relaxation times measured in step (ii) can indicate the presence of the analyte. A decrease in T2 relaxation times measured in step (iv) relative to the T2 relaxation times measured in step (ii) can indicate the presence of the analyte.

The term "analyte" or "exogenous analyte" refers to a substance or chemical constituent (e.g., glucose, folic acid, or influenza hemagglutinin peptide) in a sample (e.g., a biological or industrial fluid) that can be analyzed (e.g., detected and quantified) and monitored using the sensors described herein.

The term "subject" includes mice, rats, cows, sheep, pigs, rabbits, goats, horses, primates, dogs, cats, and humans.

A nanoparticle having at least one moiety described herein that is covalently or noncovalently linked to the nanoparticle and that can switch from being in an aggregated and disaggregated state is sometimes referred to herein as a "magnetic nanoswitch" or "nanoswitch."

Embodiments can have one or more of the following advantages.

While not wishing to be bound by theory, it is believed that nanoparticle aggregation (formation of nanoparticle aggregates, e.g., microaggregates) and disaggregation (formation of disaggregated or dispersed nanoparticles from microaggregates or nanoparticle agregates) is an equilibrium controlled process, and that the position of this equilibrium is dependent upon (and therefore maintained by) analyte concentration. When analyte concentration changes, the position of the equilibrium changes, at least in a range of sensitivity depending on several factors. This change in the position of this equilibrium is manifested by changes in proton relaxation of the water inside of the sensor chamber, which is measurable. As such, the sensors have the advantage of being useful for the continuous monitoring of changing levels of analytes because there is generally no need to re-condition or replace the sensors during the course of most ongoing (e.g., long term) measurements because essentially nothing is created or produced during detection; the equilibrium between aggregated and disaggregated nanoparticles is shifted by the analyte. As long as one can continuously monitor changes in the aforementioned equilibrium that occur inside the sensor chamber (e.g., by periodically or continuously monitoring T2 relaxation times of the water inside of the chamber), then one can continuously monitor changing levels of analytes as those changes occur.

The sensors can be used to detect a chemically diverse array of analytes, which include without limitation, carbohydrates (e.g., glucose), peptides (e.g., influenza hemagglutinin peptide), and therapeutic agents (e.g., folic acid).

The sensors are relatively simple devices lacking moving parts, electronics and any connection to an outside recording device such as a sampling tube or wire. Instead, the sensor operates by absorbing and emitting radiation at the Larmour precession frequency of water protons, which is interpretable as T2 and exogenous analyte (e.g., glucose) concentration. The radiation employed (e.g., 60 MHz for the 1.5 T MRI) penetrates biological systems, e.g., at depths where optical reporting methods can sometimes be complicated by light scattering and absorption by the tissue, e.g., tissue depths greater than about 250 μm. The sensor can therefore be essentially a remote sensor, reporting on its local environment through water relaxation measurements while unconnected to an outside recording device or power source.

Analyte detection can take place in solution rather than on a surface, so as to avoid the need for developing and optimizing sensor surface chemistry. This enables the features of an assay (sensitivity, specificity, kinetics) to be determined in a tube format, independently from the semi-permeable device or instrumentation needed to distinguish sensor water from bulk water. Binding agents, e.g., proteins and antibodies, and nanoparticles can readily be tested as reagents for new water relaxation assays, leading a panel of relaxation-based sensors for different analytes.

By sensing the position of the reversible equilibrium of nanoparticle aggregation/dispersion, the production or consumption of molecules is avoided as compared with an assay that includes irreversible reactions (e.g., single use assays). Thus, again there is no need to "recharge" the sensor with a substrate to continue operation. The sensors can be prepared for reuse, for example, by equilibrating in the absence of the analyte or under conditions chosen to mimic the absence of the analyte (e.g., relatively low concentrations of the analyte).

The radiofrequency radiation used with the water relaxation sensor interacts with water protons, rather than nanoparticles or biological molecules, thereby minimizing the likelihood of radiation induced damage.

The sensors are amenable for use in the detection of two or more analytes (e.g., a panel of different sensors each having, e.g., a different binding agent and moiety, can be used in the same screening or testing environment to detect multiple analytes).

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference in their entirety.

Although methods and materials similar or equivalent to those described herein can be used in the practice of the present invention, preferred methods and materials are described below. The materials, methods, and examples are illustrative only and not intended to be limiting. Other features and advantages of the invention will be apparent from the detailed description and from the claims.

DESCRIPTION OF DRAWINGS

FIG. 4C shows the particle size distribution for dispersed Glu-CLIO nanoparticles. FIG. 4D shows the switch from dispersed nanoparticles (dark bars) to the microaggregate state (light bars) upon ConA addition. FIG. 4E shows the switch of the Glu-CLIO nanoparticles back to the dispersed state upon glucose addition.

FIG. 6A shows sensors with ConA and Glu-CLIO placed in 50 mL tubes. FIG. 6B shows an MR image of a 50 mL tube with external glucose of 0.5 mg/mL FIG. 6C shows an MR image of with an external glucose concentration of 1.4 mg/mL. Conditions were essentially the same as described with respect to FIGS. 3A and 3B.

FIG. 8C shows the particle size distribution for dispersed HA-CLIO nanoparticles. FIG. 8D shows the switch from dispersed nanoparticles (dark bars) to the microaggregate state (light bars) upon anti-HA addition. FIG. 8E shown the switch of the HA-CLIO nanoparticles back to the dispersed state upon HA addition.

FIG. 9C shows the particle size distribution for dispersed FA-CLIO nanoparticles. FIG. 9D shows the switch from dispersed nanoparticles (dark bars) to the microaggregate state (light bars) upon anti-FA addition. FIG. 9E shows the return of the FA-CLIO nanoparticles back to the dispersed state upon FA addition.

Like reference symbols in the various drawings indicate like elements.

DETAILED DESCRIPTION

This invention relates generally to magnetic resonance-based sensors (e.g., water relaxation-based sensors) and methods for detecting various analytes (e.g., exogenous analytes) in water-containing media (e.g., in vitro or in vivo media).

Sensors

In general, the sensors described herein include magnetic nanoparticles, or nanoparticles with a magnetic moment under certain conditions, encapsulated within a semipermeable walled enclosure, e.g., an enclosure that retains the nanoparticles, but allows for passage of the analyte into and out of the confines of the sensor chamber. The walled enclosure can have one or more openings sized to enable the passage of the analyte, but not the nanoparticles (and binding agent, when present). Each of the nanoparticles has at least one moiety (e.g., a molecular fragment of the analyte being detected or a molecular fragment of a derivative, isostere, or mimic of the analyte being detected; or a protein) that is covalently or noncovalently linked to the nanoparticle. The sensor can further include a binding agent (e.g., a protein or a monoclonal antibody) also encapsulated within a semipermeable enclosure. The binding agent, when present, is capable of binding to the analyte and the moiety; and the moiety is capable of binding to the analyte or the binding agent. In general, the moiety and the analyte can each bind reversibly to the binding agent, when present; or the analyte can bind reversibly to the moiety. Currently preferred chemistries for use in the practice of the invention are described herein. Generally, the chemistry of the analyte, binding moiety, and binding agent, per se, unless indicated otherwise herein, may be and typically is conventional, and may be adapted from other arts for use in the novel sensors and methods disclosed herein.

Figure 1A:
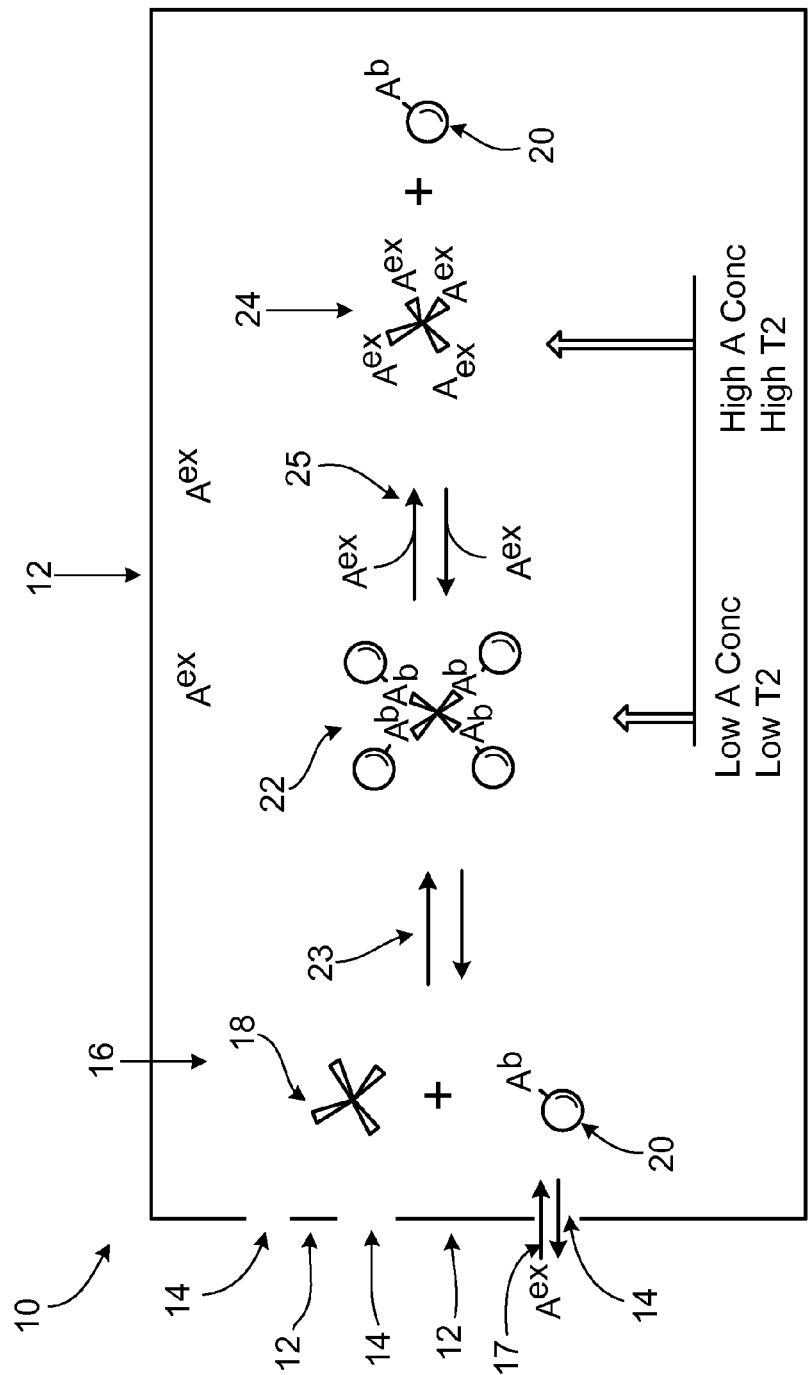
FIG. 1A is a cross-sectional view of an embodiment of a water relaxation-based sensor for detecting a monovalent analyte. Also shown are the equilibrium controlled processes that occur in the sensor chamber in the absence and presence of the analyte and a summary of the water relaxation properties of the aggregated and dispersed nanoparticles.

Referring to FIG. 1A, in some embodiments, a water relaxation-based sensor 10 for detecting a monovalent analyte ($A^{ex}$ in FIG. 1A) includes a walled enclosure 12, a plurality of nanoparticles 20, and at least one binding agent (e.g., a protein) 18. The walled enclosure encapsulates a chamber 16 and is perforated with a plurality of openings 14. Both the nanoparticles 20 and the binding agent 18 are located within the confines of the chamber 16. Each of the nanoparticles 20 has at least one moiety ($A^b$ in FIG. 1A) that is covalently or noncovalently linked to the nanoparticle and that includes a molecular fragment of the analyte being detected. The binding agent 18 is capable of binding (e.g., reversibly binding) to the analyte and the moiety $A^b$. In all embodiments, the analyte is smaller in size than either the nanoparticles 20 or the binding agent 18. In all embodiments, the openings 14 are (i) larger in size than the analyte so as to allow the analyte to pass freely into and out of the chamber 16 (arrows 17) and (ii) smaller in size than either the nanoparticles 20 or the binding agent 18 so as to retain the nanoparticles 20 and the binding agent 18 within the chamber 16.

When the analyte is absent, the nanoparticles 20 bind to the binding agent 18 to form a nanoparticle aggregate 22 within the sensor chamber 16. It is believed that binding of the nanoparticles 20 to the binding agent 18 occurs through the moiety $A^b$ (see FIG. 1A). In general, formation of the nanoparticle aggregate 22 is an equilibrium controlled process (arrows 23).

When the exogenous analyte is present and enters the chamber 16 through opening 14, the binding agent-bound (e.g., binding protein-bound) nanoparticles of aggregate 22 are displaced from the binding agent by the analyte ($A^{ex}$ in FIG. 1A), thereby altering the nanoparticle-binding agent (binding protein) equilibrium (arrows 23). As a result, a second equilibrium is established (arrows 25) in the chamber 16 among the analyte, s analyte-binding agent (binding protein complex 24, and (regenerated) nanoparticles 20. The regenerated nanoparticles produced in the second equilibrium controlled process (arrows 25) are substantially disaggregated relative to the bound nanoparticles of aggregate 22 formed in the first equilibrium controlled process (arrows 23).

Figure 1B:
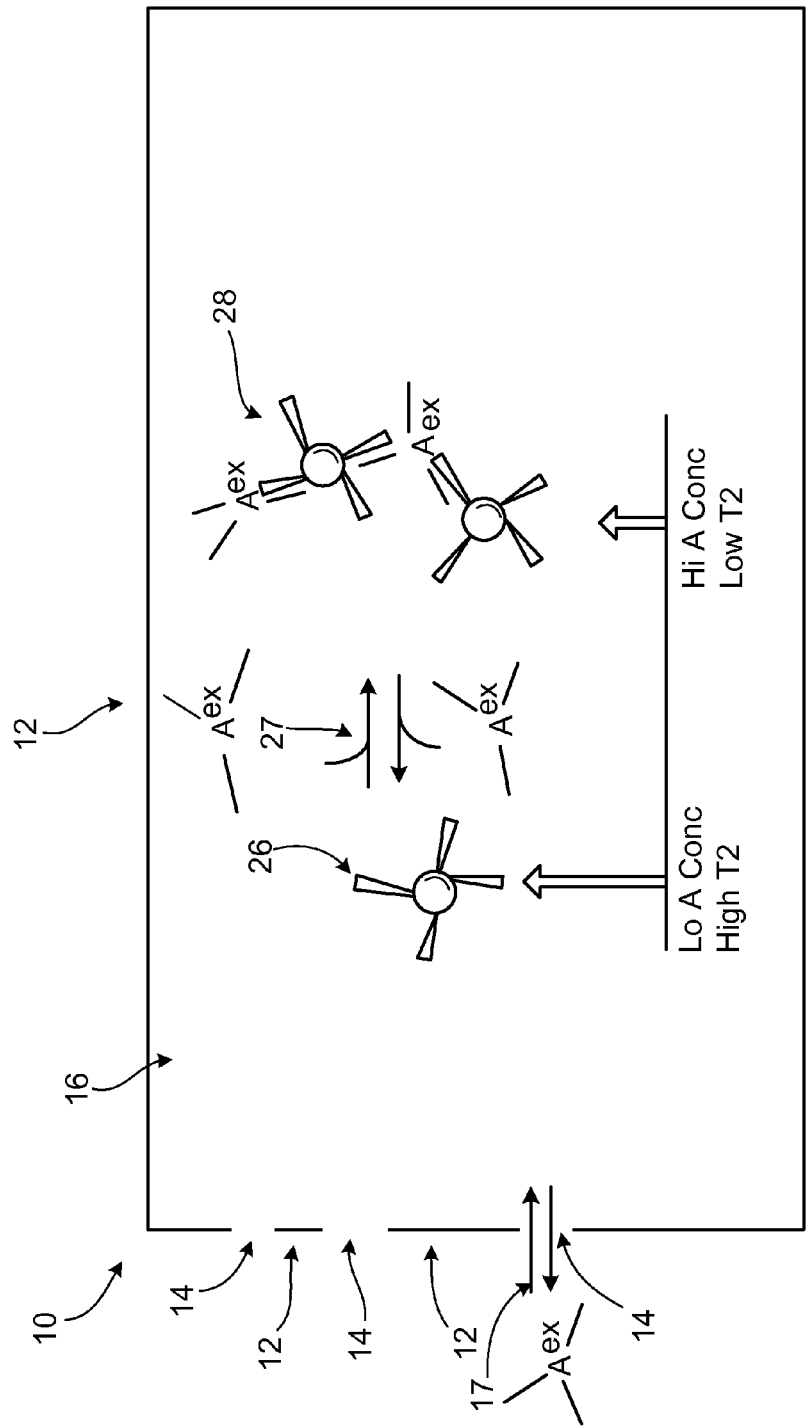
FIG. 1B is a cross-sectional view of an embodiment of a water relaxation-based sensor for detecting a monovalent analyte. Also shown are the equilibrium controlled processes that occur in the sensor chamber in the absence and presence of the analyte and a summary of the water relaxation properties of the aggregated and dispersed nanoparticles.

Referring to FIG. 1B, in some embodiments, a water relaxation-based sensor 10 for detecting a multivalent analyte ($\equiv A^{ex}$ in FIG. 1B) includes a walled enclosure 12 as described elsewhere and a plurality of nanoparticles 26. The nanoparticles are located within the confines of the chamber, and each of the nanoparticles has at least one moiety (e.g., at least one protein; at least 2, at least 3, at least 4) that is linked to the nanoparticle (hollow wedges in FIG. 1B). In all embodiments, the exogenous analyte is smaller in size than the nanoparticles 26. In all embodiments, the openings 14 are (i) larger in size than the exogenous analyte so as to allow the analyte to pass freely into and out of the chamber 16 (arrows 17) and (ii) smaller in size than the nanoparticles 26 so as to retain the nanoparticles 26 within the chamber 16.

When the analyte is absent, the nanoparticles 26 are substantially disaggregated within the sensor chamber 16.

When the analyte is present and enters the chamber 16 through opening 14, the nanoparticles 26 bind to the multivalent analyte ($\equiv A^{ex}$ in FIG. 1B) to form a nanoparticle aggregate 28 within the chamber (arrows 27). The nanoparticles that form part of aggregate 28 are substantially aggregated relative to nanoparticles 26. It is believed that binding of the nanoparticles 26 to the analyte occurs through the moiety (e.g., a protein). In general, formation of the nanoparticle aggregate 28 is an equilibrium controlled process (arrows 27).

Figure 1C:
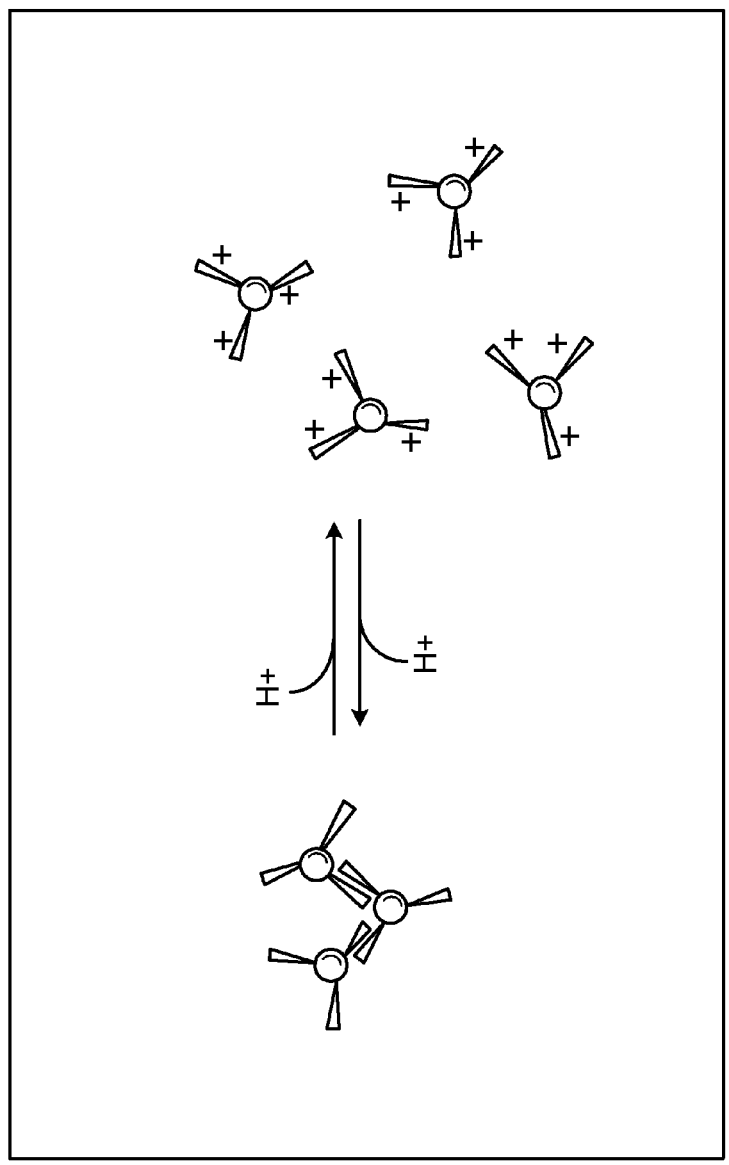
FIG. 1C is a schematic representation of a sensor configuration embodiment in which the nanoparticles can bind directly to each other, and the analyte can mediate aggregation/disaggregation. The surface of this nanoparticle (left side of equation) is capable of binding to an analyte and binding of the analyte can alter the physical properties of the surface, e.g., charge or hydrophobicity, resulting in aggregation/disaggregation (right side of equation). Here, aggregation/disaggregation is mediated by changes in pH (H+).

Referring to FIG. 1C, in some embodiments, the sensors can be configured such that an analyte (e.g., a proton, $H^+$) can directly mediate self-assembly (aggregation and disaggregation of the nanoparticles). Sensors having the configuration shown in FIG. 1C can have one or more of the following properties: (i) the nanoparticles can bind directly to each other (i.e., there are no molecules serving a "bridges" between nanoparticles, as shown in FIGS. 1A and 1B); (ii) a single type of nanoparticle can be employed, and (iii) an analyte can control the self-assembly by binding to the surface of the nanoparticle. In these embodiments, the surface of the nanoparticle is capable of binding to an analyte. Binding of the analyte can alter the physical properties of the surface, e.g. charge or hydrophobicity. While not wishing to be bound by theory, it is believed that the change in surface properties can alter the attraction between the nanoparticles, and self-assembly (or disassembly) of nanoparticles can occur. In certain embodiments, the surface of the nanoparticle can be designed to have a surface that can be charged or uncharged, as the pH is varied over some range of interest. For example, a peptide such as Ac-LLLLLL-KHHHE-G-K(FITC)—C—$NH_2$, pI=6.48, can be attached to nanoparticles using bifunctional crosslinking agents such as SPDP or SIA, (see, e.g., Koch et al. "Uptake and metabolism of a dual fluorochrome Tat-nanoparticle in HeLa cells." *Bioconjug Chem.* 2003; 14(6):1115). At a pH of about 6.48 or above, the histidine is substantially unprotonated, and aggregation can occur through self-association among the hydrophobic leucine side chains. At a pH below about 6.48, the histidine is substantially protonated, the nanoparticles carry a positive charge and are dispersed.

Figure 1D:
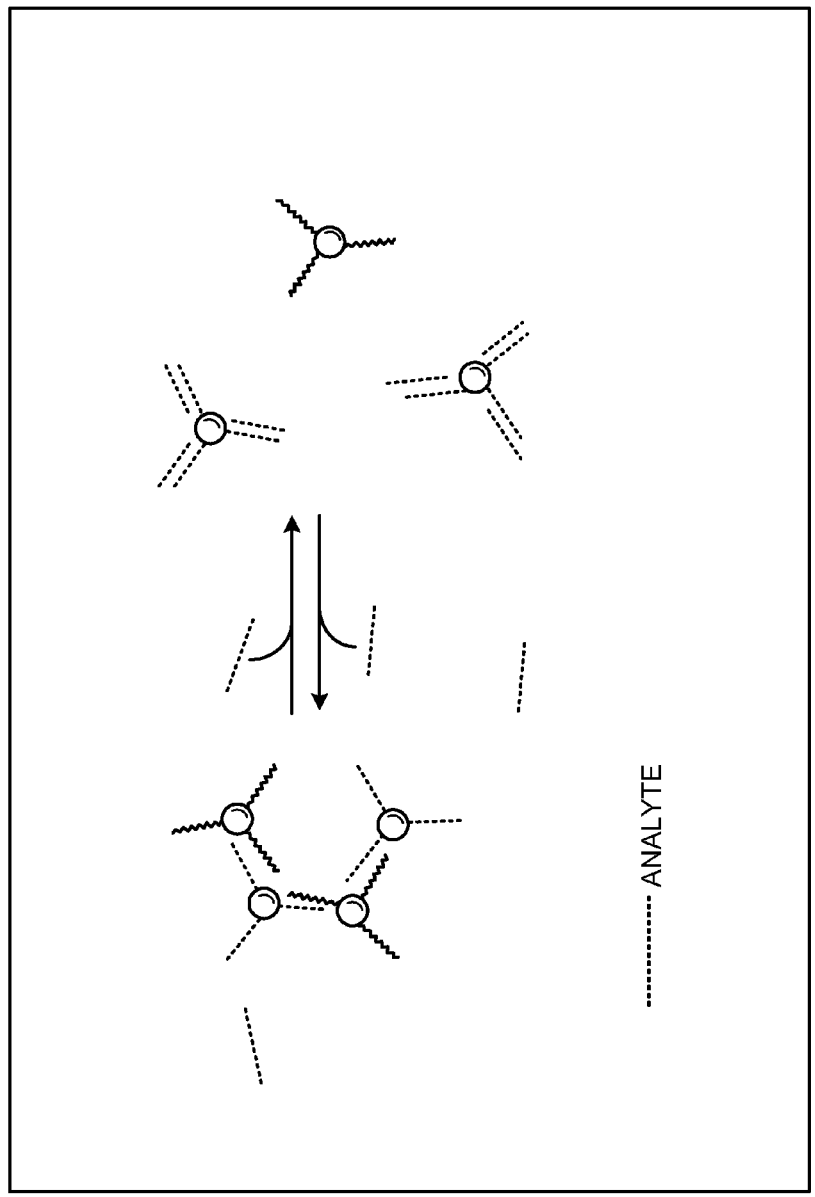
FIG. 1D is a schematic representation of a sensor configuration embodiment in which the detection of a sequence of bases on a nucleic acid fragment can mediate self-assembly of the nanoparticles. When the two types of nanoparticles are mixed, they can self-assemble via the hybridization that occurs between bases of the oligonucleotides (left side of equation). An analyte that can bind to one of the types of particles can induce the dissociation of aggregates (right side of equation).

Referring to FIG. 1D, in some embodiments, the sensors can be configured such that detection of a sequence of bases on a nucleic acid fragment can mediate self-assembly of the nanoparticles. Sensors having the configuration shown in FIG. 1D can have one or more of the following properties: (i) two types nanoparticles can be prepared which have an affinity for each other, and (ii) one of the two types of nanoparticles is capable of binding the analyte. In these embodiments, two types of nanoparticles can be synthesized, each having a specific sequence of synthetic oligonucleotide attached. When the two types of nanoparticles are mixed, they can self-assemble via the hybridization that occurs between bases of the oligonucleotides. An example of such double-stranded, oligonucleotide-mediated, nanoparticle aggregate is given in Perez et. al., "DNA-based magnetic nanoparticle assembly acts as a magnetic relaxation nanoswitch allowing screening of DNA-cleaving agents." *J Am Chem. Soc.* 2002; 124:2856. An analyte (e.g. a sequence of bases present on a nucleic acid fragment) can then enter the sensor and by binding to one of the types of particles can induce the dissociation of aggregates.

Since the concentration dependent reaction of the analyte with the nanoparticle aggregate alters the nanoparticle aggregation state, the presence and quantity of the exogenous analyte can be sensed, for example, as a change in the T2 relaxation times of water inside of the sensor chamber. It is known, for example, that water T2 relaxation times shorten upon aggregation or clustering of previously dispersed (e.g., monodispersed, polydispersed) magnetic nanoparticles. While not wishing to be bound by theory, it is believed that during nanoparticle self-assembly into higher order nanoassemblies, the superparamagnetic iron oxide core of individual nanoparticles becomes more efficient at dephasing the spins of the surrounding water protons (i.e., enhancing spin-spin relaxation times, e.g., T2 relaxation times).

Thus, in some embodiments, the analyte can be detected and quantified in the sampling media by monitoring the relaxation properties of the water that is present within the sensor chamber 16 (e.g., measuring changes, e.g., increases and decreases, in T2 relaxation times of water that is present within the sensor chamber). For example, referring to FIG. 1A, the T2 relaxation times of the water inside of the sensor chamber 16 are expected to decrease in the absence of analyte (due to formation of the nanoparticle aggregate 22) and then increase relative to these depressed values in the presence of analytes (due to displacement and subsequent disaggregation of the bound nanoparticles of aggregate 22). Alternatively, referring to FIG. 1B, the T2 relaxation times of the water inside of the sensor chamber 16 are expected to increase in the absence of multivalent analyte and then decrease relative to these values in the presence of the multivalent analytes. Since the binding agent and/or the nanoparticles are confined within the chamber 16, the changes in nanoparticle aggregation occurring within the sensor chamber 16 in general do not substantially alter the proton relaxation of water outside of the chamber (i.e., bulk water).

Although measuring T2 can be a desirable method for determining nanoparticle aggregation, any water relaxation phenomena associated with nanoparticles or with their change in aggregation state can be used. T2 can generally be determined in a relatively fast and facile manner. However, measurements of nanoparticle aggregation can use T2 in conjunction with other relaxation processes such as T1. Measurements of T1 and T2 can be used to correct for small changes in nanoparticle aggregation state within the sensor, due to a small expansion of contraction of the chamber. Accordingly, as used herein, references to measurement of relaxation phenomenon or magnetic relaxivity is intended to embrace all such relaxation related processes, including measurement of T1.

Sensor Components and Specifications

In general, the size and shape of the sensor 10 can be selected as desired.

In some embodiments, the sensors can be, for example, tubular, spherical, cylindrical, or oval shaped. The sensors described herein can have other shapes as well.

In some embodiments, the size and shape of the sensor can be selected to accommodate a desired or convenient sample holder size and/or sample volume (e.g., in in vitro sensing applications). In general, the volume of sensor can be selected to enable the sensor to distinguish between the relaxation properties of water inside of the chamber and the water outside of the chamber. For example, the sensor size can be selected so as to accommodate a sample volume of from about 0.1 microliters (µL) to about 1000 milliliters (mL) (e.g., about 1 µL (e.g., with animal imagers), 10 µL (e.g., with clinical MRI instruments) or 0.5 mL. In certain embodiments, the sensor can have a tubular shape in which the open end of the tube has a diameter of from about 1 millimeter (mm) to about 10 mm (e.g., 5 mm 7.5 mm).

In some embodiments, the sensor size and shape can be selected on the basis of the spatial resolution capabilities of conventional magnetic resonance technology (e.g., in in vitro sensing applications). In certain embodiments, the longest dimension of the sensor can be from about 0.01 mm to about 2 mm (e.g., 0.05, 0.1, 0.2, 0.3, 0.4, 0.5, 0.6, 0.7, 0.8, 0.9, 1). In certain embodiments, the applied magnetic field can be, for example, about 0.47 Tesla (T), 1.5 T, 3 T, or 9.4 T (animal assays generally).

The walled enclosure 12 separates the chamber 16 from the bulk sample media and provides one or more conduits (e.g., openings 14) for entry of the exogenous analyte (if present) from the bulk sample media. In general, the walled enclosure 12 can be any semipermeable material (e.g., a biocompatible semipermeable material) that is permeable to the exogenous analyte and water and substantially impermeable to the nanoparticles and the binding agent. In some embodiments, the semipermeable material can be an ultrafiltration or dialysis membrane. In some embodiments, the semipermeable material can be a polymeric substance (e.g., polymeric substances used for encapsulating transplanted cells, see, e.g., M. S. Lesney, *Modern Drug Discovery* 2001, 4, 45). In some embodiments, the semipermeable material can be a material used in small implantable, sustained release devices (e.g., those used in implantable, sustained release birth control devices, e.g., Depo-Provera, Norplant, Progestasert; or those described in C. I. Thompson et al., *Can J Physiol Pharmacol* 80, 180-92 (March, 2002) or D. C. Stoller, S. R. Thornton, F. L. Smith, *Pharmacology* 66, 11-8 (September, 2002)).

In some embodiments, the walled enclosure is relatively resistant to fouling or coating under the sampling conditions, thereby increasingly the likelihood that the walled enclosure can maintain the specified pore size of the openings 14 (e.g., increasing the likelihood that openings 14 will remain substantially unblocked during sensing). Fouling is the closure of pores (e.g., openings 14) due to the adsorption of protein that blocks pore. Fouling can be ascertained by placing materials in biological fluids (e.g., blood) and evaluating their performance using biocompatibility testing methods known in the art.

In some embodiments, the walled enclosure 12 can be essentially nonimmunogenic, thereby minimizing the likelihood of causing unwanted immune or toxic side effects in a subject (e.g., a human).

Examples of biocompatible, semipermeable materials include without limitation polysaccharide based materials (cellulose), modified carbohydrate (cellulose ester), or polyvinyl pyrrolidine.

In some embodiments, the walled enclosure 12 can be made of a relatively inflexible semipermeable material, meaning that the encapsulated chamber 16 is a true space or void that does not substantially change in volume when contacted with the fluid sample media. In other embodiments, the walled enclosure can be a relatively flexible semipermeable material, meaning, for example, that the encapsulated chamber can expand in volume when contacted with the fluid sample media (e.g., by intake of the fluid sample media).

In general, the walls of the enclosure 12 are sufficiently thin to allow rapid sensor equilibration to changes in exogenous analyte levels. In some embodiments, the membrane that forms the wall can have a thickness of from about 1 and about 500 hundred microns.

In general, the pore size of the openings 14 can be selected so as to meet the molecular exclusion criteria described herein (i.e., permeable to the exogenous analyte and water and substantially impermeable to the nanoparticles and the binding agent).

In some embodiments, molecular exclusion can be exclusion by molecular weight. In certain embodiments, each of the openings can have a pore size of from about 1 kDa to about 500,000 kDa (e.g., a pore size that allows passage of molecules that have a certain molecular weight Each of the openings can have a size (pore size) of from about 1 kDa to about 1 µm (e.g., about 1 kDa to about 300,000 kDa; about 1 kDa to about 100,000 kDa; about 1 kDa to about 5 kDa; 1 kDa to about 3 kDa; 1 kDA to about 1 µm). In certain embodiments, the openings can have a pore size of about 1 kDa or about 3 kDa.

In certain embodiments, the semipermeable material can be Spectra/Por® tubing, Slide-A-Lyzer® microcassettes or dialysis fibers. Such materials are generally preferred for applications not involving implantation. In general, the semipermeable material has a pore size that is larger in size than the analyte to permit passage of the analyte into and out of the chamber, but sufficiently small to retain magnetic nanoparticles and other reagents such as binding agents (e.g., a binding protein) within the confines of the chamber. The semipermeable material can be selected for the stability (long term function) in the fluid, which contains the analyte to be measured (e.g., blood plasma, interstitial fluid, cerebral spinal fluid of a human or animal subject). The semipermeable material can be further selected on the basis of whether the sensor is implanted or whether the fluid to be assayed is contained within a vessel that is outside of the subject (e.g., a bioreactor, tube or pipe).

The magnetic particles can be nanoparticles (e.g., having a particle size of from about 10 nanometers (nm) to about 200 nm) or particles (e.g., having a particle size of from about 200 nm to about 5000 nm) provided that the particles remain essentially suspended (i.e., the particles do not settle). As used herein, the term "magnetic nanoparticles" refers to any particle that is always magnetic and any particle that has a magnetic moment under certain conditions (e.g., in an applied electromagnetic field). Particle settling can generally be avoided by using relatively small particles (e.g., nanoparticles) or relatively large particles whose density is comparable to that of water. The density of particles can be altered by using polymers of different densities in their synthesis. In all embodiments, the nanoparticles or particles have a surface that permits the attachment of biological molecules. In some embodiments, the magnetic particles can be nanoparticles having a particle size of from about 10 nm to about 500 nm (e.g., about 15 to about 200 nm, about 20 to about 100 nm, about 10 nm to about 60 nm, about 20 nm to about 40 nm, about 30 nm to about 60 nm, about 40 to 60 nm; or about 50 nm). The unfunctionalized metal oxides are generally crystals of about 1-25 nm, e.g., about 3-10 nm, or about 5 nm in diameter.

Magnetic materials larger than nanoparticles (particles) can be used. In general, such particles can have one or more of the following properties: (i) it is desirable that the particles have a relatively high R2, i.e., alter water relaxation, (ii) it is desirable that the particles not to have a high susceptibility to settle significantly by gravity during the time course of the assay, (iii) it is desirable that the particles have a surface for the attachment of biomolecules, preferably amino or carboxyl groups. Examples include microspheres of from about 1-5 micron in diameter. Such particles can be obtained, e.g., from commercial suppliers, which include Dynbead magnetic microspheres from Invitrogen (Carlsbad, Calif.), microspheres from Bangs Laboratories (Fishers, Ind.), and Estapor® Microspheres from Merck or EMD Life Sciences (Naperville, Ill.).

In some embodiments, the particles (e.g., nanoparticles 20 or 26) can be unfunctionalized magnetic metal oxides, such as superparamagnetic iron oxide. The magnetic metal oxide can also include cobalt, magnesium, zinc, or mixtures of these metals with iron. The term "magnetic" as used herein means materials of high positive magnetic susceptibility such as paramagnetic or superparamagnetic compounds and magnetite, gamma ferric oxide, or metallic iron. In some embodiments, the nanoparticles 20 include those having a relatively high relaxivity, i.e., strong effect on water relaxation.

In general, the particles can have a relatively high relaxivity owing to the superparamagnetism of their iron or metal oxide. In some embodiments, the nanoparticles (e.g., 20 or 26) have an R1 relaxivity between about 5 and 30 mM$^{-1}$ sec$^{-1}$, e.g., 10, 15, 20, or 25 mM$^{-1}$ sec$^{-1}$. In some embodiments, the nanoparticles (e.g., 20 or 26) have an R2 relaxivity between about 15 and 100 mM$^{-1}$ sec$^{-1}$, e.g., 25, 50, 75, or 90 mM$^{-1}$ sec$^{-1}$. In some embodiments, nanoparticles (e.g., 20 or 26) have a ratio of R2 to R1 of between 1.5 and 4, e.g., 2, 2.5, or 3. In some embodiments, the nanoparticles (e.g., 20 or 26) have an iron oxide content that is greater than about 10% of the total mass of the particle, e.g., greater than 15, 20, 25 or 30 percent.

In some embodiments, when the magnetic nanoparticle is an iron oxide-based nanoparticle, concentrations of iron (Fe) can be from about 2 micrograms (µg)/mL to about 50 µg/mL Fe. In general, the iron concentration is selected so as to be sufficiently high to alter the relaxation properties of water. For particles with relatively high relaxivities, lower iron concentrations can be used. For particles with relatively low relaxivities, higher iron concentrations can be used.

Each of the nanoparticles (e.g., 20 or 26) includes at least one moiety (e.g., at least 2, at least 3, at least 4) that is covalently or noncovalently linked to the nanoparticle.

In some embodiments, the moiety can be linked to the nanoparticle via a functional group. The functional group can be chosen or designed primarily on factors such as convenience of synthesis, lack of steric hindrance, and biodegradation properties. Suitable functional groups can include —O—, —S—, —SS—, —NH—, —NHC(O)—, —(O)CNH—, —NHC(O)(CH$_2$)$_n$C(O)—, —(O)C(CH$_2$)$_n$C(O)NH—, —NHC(O)(CH$_2$)$_n$C(O)NH—, —C(O)O—, —OC(O)—, —NHNH—, —C(O)S—, —SC(O)—, —OC(O)(CH$_2$)$_n$(O)—, —O(CH$_2$)$_n$C(O)O—, —OC(O)(CH$_2$)$_n$C(O)—, —C(O)(CH$_2$)$_n$C(O)O—, —C(O)(CH$_2$)$_n$C(O)—, —NH(CH$_2$)$_n$C(O)—, —C(O)(CH$_2$)$_n$NH—, —O(CH$_2$)$_n$C(O)—, —C(O)(CH$_2$)$_n$O—, —S(CH$_2$)$_n$C(O)—, —C(O)(CH$_2$)$_n$S—, —NH(CH$_2$)$_n$—, —(CH$_2$)$_n$NH—, —O(CH$_2$)$_n$—, —(CH$_2$)$_n$O—, —S(CH$_2$)$_n$—, or —(CH$_2$)$_n$S—, in which each n can be 1-100 (e.g., n can be 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, 99). Functional groups having cyclic, unsaturated, or cyclic unsaturated groups in place of the linear and fully saturated alkylene linker portion, (CH$_2$)$_n$, can also be used to attach the moiety to the nanoparticle. In certain embodiments, the functional group can be selected so as to render the nanoparticle larger in size than the opening(s) in the wall of the chamber so as to retain the nanoparticle within the confines of the chamber (e.g., where a relatively large analyte is being detected such as a lipoprotein).

In certain embodiments, the functional group can be —NHC(O)(CH$_2$)C(O)NH—, in which n can be 0-20. In certain embodiments, n can be 2, 3, 4, 5, or 6 (preferably, 2).

The functional group can be present on a starting material or synthetic intermediate that is associated with either the nanoparticle portion or the moiety portion of the nanoparticles (e.g., 20 or 26).

In some embodiments, a nanoparticle-based starting material can contain one or more functional groups for attachment of one or more moieties, (e.g., 2, 4, 6, 8, 10, 15, 20, 25, 30, 35, 40, 45, or 50 functional groups). In certain embodiments, the nanoparticle can be an amino-derivatized cross-linked iron oxide nanoparticle (e.g., NH$_2$-CLIO). The number of moieties (e.g., a molecular fragment of the analyte being detected or a molecular fragment of a derivative, isostere, or mimic of the analyte being detected; or a protein) that are ultimately linked to the nanoparticle can be equal to or less than the number of functional groups that are available for attachment of the moiety(ies) to the nanoparticle. In any event, it is permissible for the number of moieties per nanoparticle to vary within a given population of nanoparticles (e.g., a population of 20 and/or 26).

In general, the number of moieties per nanoparticle can be selected as desired (e.g., depending on the number and location of binding sites on the binding agent (e.g., a protein) and/or if it is desired to have the nanoparticle cross link binding agents (e.g., proteins) when more than one binding agent is present). In some embodiments, the magnetic particles can be multivalent particles in which multiple copies of a monovalent material are attached to the same particle. In general, the valency can be from about 2.5 to about 20 copies of bound moiety per nanoparticle (i.e., average numbers of copies per nanoparticle, thus some particles can be monovalent within a given population of generally multivalent particles). Higher levels are not necessarily believed to be needed for function. Multivalent nanoparticles can be prepared by attaching two or more functional groups per nanoparticle. Multivalent nanoparticles can also be prepared by attaching either multivalent or monovalent binding agents (e.g., proteins).

In general, moieties can include, without limitation, carbohydrates (e.g., glucose, polysaccharides), antibodies (e.g., monoclonal antibodies, biotinylated anti-GFP polyclonal antibody), amino acids as well as derivatives and stereoisomers thereof (e.g. D-phenylalanine), chiral moieties, lipids, sterols, lipopolysaccharides, lipoproteins, nucleic acids, oligonucleotides, therapeutic agents (e.g., folic acid), metabolites of therapeutic agents, peptides (e.g., influenza hemagglutinin peptide), or proteins.

In some embodiments, the moiety can be, or include as part of its chemical structure, a molecular fragment of the analyte being detected or a molecular fragment of a derivative, isostere, or mimic of the analyte being detected.

In general, such a moiety is one that is (i) recognized by the binding agent (e.g., protein, e.g., a binding protein) and (ii) displaceable from the binding agent by the analyte (i.e., the analyte can compete with the moiety for binding to the binding agent (e.g., a protein)). Thus, in some embodiments, the moiety and the analyte being detected can be substantially similar in structure to one another and have substantially similar binding affinities towards the binding agent. In other embodiments (such as when the moiety is, or includes as part of its chemical structure, a molecular fragment of a derivative, isostere, or mimic of the analyte being detected), the moiety and the analyte being detected may not necessarily be substantially similar in structure, but may have substantially similar binding affinities towards the binding agent.

Nanoparticles having at least one moiety that is a molecular fragment of the analyte being detected or a molecular fragment of a derivative, isostere, or mimic of the analyte being detected can have the general formula (A):

$$(A)_z\text{-NP}^c \quad\quad (A)$$

in which:

moiety "A" is a molecular fragment of an analyte (or a derivative, isostere, or mimic thereof), A-X, wherein X is a hydrogen atom or a functional group that is present in the free analyte (or a derivative, isostere, or mimic thereof), but not incorporated into the nanoparticle of formula (A);

"NP$^c$" is the nanoparticle core;

"-" is a covalent linkage (e.g., a chemical bond or any linking functional group described herein) that connects any atom of the fragment to the nanoparticle; and z is 1-50 (e.g., 1-40, 1-30, 1-25, 1-20, 2-20, 2, 4, 6, 8, 10, and 15).

In certain embodiments, X can be a hydrogen atom that forms part of an amino or hydroxy group that is present in the analyte; or X can be functional group, such as an amino group or a hydroxy group. By way of example, for a given analyte A-OH (X=OH=hydroxy group), the corresponding nanoparticle can have, for example and without limitation, the structure $(A\text{-O})_z\text{---NP}^c$ or $(A\text{-NH})_z\text{---NP}^c$.

In some embodiments, the moiety can include a carbohydrate as part of its chemical structure (e.g., glucosyl). In certain embodiments, the moiety can include a molecular fragment of a carbohydrate analyte being detected or a molecular fragment of a derivative, isostere, or mimic of a carbohydrate analyte being detected. For example, the moiety can have formula (I):

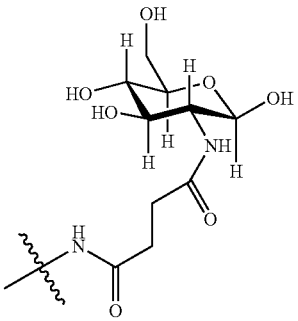

(I)

in which the wavy line indicates the point of connection of the moiety to the nanoparticle. The moiety of formula (I) can be used in conjunction with a sensor for detecting and quantifying glucose.

The moiety can be a monovalent or multivalent protein (e.g., having at least two (e.g., three, four, five, or six)) binding sites.

In certain embodiments, the nanoparticle can further include a substituent that serves to render the nanoparticle larger in size than the opening(s) in the wall of the chamber so as to retain the nanoparticle within the confines of the chamber (e.g., where a relatively large analyte is being detected such as a lipoprotein).

In some embodiments, the binding agent can be absent (e.g., when detecting multivalent analytes with nanoparticles in which the covalently or noncovalently linked moiety is, e.g., a protein; see, e.g., assay configuration delineated in FIG. 1B). Thus the assay can measure multivalent analyte proteins, using a sensor with a pore size that is large enough to allow analyte to enter and leave the chamber, while retaining nanoparticles, i.e. the pore size in FIG. 1A and FIG. 1B. can be adjusted. Various assay configurations are described herein.

In some embodiments, the binding agent can be present (e.g., when detecting monovalent analytes with nanoparticles, which include a molecular fragment of the analyte being detected or a molecular fragment of a derivative, isostere, or mimic of the analyte being detected; see, e.g., assay configuration delineated in FIG. 1A). The binding agent can be, for example, a protein, an antibody, a lectin, a receptor binding protein, a binding domain of a protein, a synthetic material, or a non-protein material.

In some embodiments, the binding agent can be a protein. In certain embodiments, the binding protein can be a multivalent binding protein having at least two binding sites (e.g., three, four, five, or six).

In general, binding between the binding agent (e.g., a protein or antibody) and the nanoparticle (via the moiety) and the analyte is reversible; and binding between a moiety and an analyte is reversible. As such, the analyte can be detected and quantified in a non-consumptive manner (i.e., the binding agent or the moiety reversibly binds, but does not consume, the analyte). This reversibility provides a steady state condition for bound and unbound analyte that can be quantitated. Analyte concentration can then be mathematically calculated using conventional methods. A person of ordinary skill in the art would recognize that, for example, the reaction kinetics associated with binding and release of the analyte can be different for each protein selected as a binding agent.

In certain embodiments, the protein binding agent can bind a therapeutic agent or metabolite thereof; a carbohydrate (e.g., glucose; e.g., the protein can be conconavalin A); or an amino acid (e.g., the binding protein can selectively bind one enantiomer over another, e.g., D-alanine versus L-alanine). In certain embodiments, the protein can be green fluorescent protein (GFP).

In certain embodiments, the protein binding agent can be a monomer. In other embodiments, the protein binding agent can be multimeric binding agent (e.g., prepared by making a fusion protein that includes several copies of one protein or cross-linking monomers to create a multivalent binding moiety). In still other embodiments, the binding agent can be an enzyme, which is modified so that it can bind to a substrate, but does not catalyze a reaction.

In certain embodiments, the binding agent can bind a lipid, a sterol, a lipopolysaccharide, or a lipoprotein. For example, the binding agent can be a protein that binds a sterol (e.g., apoSAAp for binding cholesterol, see, e.g., Liang and Sipe, 1995, "Recombinant human serum amyloid A (apoSAAp) binds cholesterol and modulates cholesterol flux", J. Lipid Res, 36(1): 37). As another example, the binding agent can be a receptor that binds a lipoprotein (e.g., a soluble low density lipoprotein and/or mutants thereof, see, e.g., Bajari et al, 2005, "LDL receptor family: isolation, production, and ligand binding analysis", Methods, 36:109-116; or Yamamoto et al., 2005, "Characterization of low density lipoproteinreceptor ligand interactions by fluorescence resonance energy transfer", J. Lipid Research, 47:1091. As a further example, the binding agent can be a protein that binds a fatty acid (e.g., human serum albumin, see, e.g., Fang et al, 2006, "Structural changes accompanying human serum albumin's binding of fatty acids are concerted", 1764(2):285-91. Epub 2005 Dec. 27).

In other embodiments, the binding agent can be a monoclonal antibody, a polyclonal antibody, or a oligonucleotide. The binding agent can be, e.g., an antibody to folic acid or an antibody to influenza hemagglutinin peptide.

In some embodiments, the analyte can be chiral. The chiral analyte can be present together with one or more optically active moieties in the sample (e.g., a stereoisomer of the chiral analyte in the sample, e.g., the enantiomer of the chiral analyte in the sample). In certain embodiments, the chiral analyte can be an amino acid.

The sensors described herein can be used to detect, monitor, and quantify a of analytes that can include, without limitation, ions, small molecules, proteins, viruses and lipoproteins (see Table 1).

TABLE 1

Analytes that can be measured by water relaxation sensors

| Analyte | Type of analyte (size in kDa unless otherwise noted) |
|---|---|
| T4, T3, cortisol | Small molecule hormone (<1) |
| Thyroid stimulating hormone (TSH), human chorionic gonadotropin (hCG), leutinizing hormone (LH), follicle stimulating hormone (FSH) | Protein hormones (10-100) |
| Troponin, C-reactive protein (CRP), Creatine phosphokinase (CPK-MB, CPK-BB), myoglobin | Proteins for inflammation or heart attack (10-100) |
| Prostatic specific antigen (PSA), Carcinoma embryonic antigen (CEA), alphafetoprotein (AFP) | Proteins for cancer detection (10-100) |
| Low density lipoprotein (LDL), high density lipoprotine (HDL) | Lipoproteins for lipid status (500-2000) |
| Ferritin | Protein for iron anemia (400-600) |

TABLE 1-continued

Analytes that can be measured by water relaxation sensors

| Analyte | Type of analyte (size in kDa unless otherwise noted) |
|---|---|
| Paclitaxel | Small molecule cancer chemotherapeutic (<1) |
| B12/Folate | Small molecule nutrients and cofactors |
| Theophyline, gentamycin, tobramycin, valproate | Therapeutic drug (<1) |
| Digoxin, digitoxin | Therapeutic drug (<1) |
| Glucose | Glucose (<1) |
| Hydrogen ions | Metabolite (<1) |
| Calcium ion | Metabolite (<1) |
| Herpes simplex virus | Virus (1 µm) |
| Human immunodeficiency virus (HIV) | Virus (1 µm) |
| Hepatitis A, B or C | Virus (1 µm) |

In certain embodiments, the analyte can be a carbohydrate (e.g., glucose); a lipid, a sterol, a lipopolysaccharide, a lipoprotein, a nucleic acid or an oligonucleotide; therapeutic agents (e.g., folic acid), metabolites of therapeutic agents, peptides (e.g., influenza hemagglutinin peptide), or a protein.

Sensor Manufacture and Use

In some embodiments, nanoparticles having reactive functional groups, (e.g., electrophilic functional groups such as carboxy groups or nucleophilic groups such as amino groups) can be employed as starting materials for the nanoparticles used in conjunction with the sensors.

Carboxy functionalized nanoparticles can be made, for example, according to the method of Gorman (see WO 00/61191). In this method, reduced carboxymethyl (CM) dextran is synthesized from commercial dextran. The CM-dextran and iron salts are mixed together and are then neutralized with ammonium hydroxide. The resulting carboxy functionalized nanoparticles can be used for coupling amino functionalized groups, (e.g., a further segment of the functional group or the substrate moiety).

Carboxy-functionalized nanoparticles can also be made from polysaccharide coated nanoparticles by reaction with bromo or chloroacetic acid in strong base to attach carboxyl groups. In addition, carboxy-functionalized particles can be made from amino-functionalized nanoparticles by converting amino to carboxy groups by the use of reagents such as succinic anhydride or maleic anhydride.

Nanoparticle size can be controlled by adjusting reaction conditions, for example, by using low temperature during the neutralization of iron salts with a base as described in U.S. Pat. No. 5,262,176. Uniform particle size materials can also be made by fractionating the particles using centrifugation, ultrafiltration, or gel filtration, as described, for example in U.S. Pat. No. 5,492,814.

Nanoparticles can also be synthesized according to the method of Molday (Molday, R. S, and D. MacKenzie, "Immunospecific ferromagnetic iron-dextran reagents for the labeling and magnetic separation of cells," J. Immunol. Methods, 1982, 52(3):353-67, and treated with periodate to form aldehyde groups. The aldehyde-containing nanoparticles can then be reacted with a diamine (e.g., ethylene diamine or hexanediamine), which will form a Schiff base, followed by reduction with sodium borohydride or sodium cyanoborohydride.

Dextran-coated nanoparticles can be made and cross-linked with epichlorohydrin. The addition of ammonia will react with epoxy groups to generate amine groups, see, e.g., Josephson et al., *Angewandte Chemie, International Edition* 40, 3204-3206 (2001); Hogemann et al., *Bioconjug. Chem.*, 2000, 11(6):941-6; and Josephson et al., "High-efficiency intracellular magnetic labeling with novel superparamagnetic-Tat peptide conjugates," *Bioconjug. Chem.,* 1999, 10(2):186-91. This material is known as cross-linked iron oxide or "CLIO" and when functionalized with amine is referred to as amine-CLIO or $NH_2$-CLIO.

Carboxy-functionalized nanoparticles can be converted to amino-functionalized magnetic particles by the use of water-soluble carbodiimides and diamines such as ethylene diamine or hexane diamine.

Figure 2:
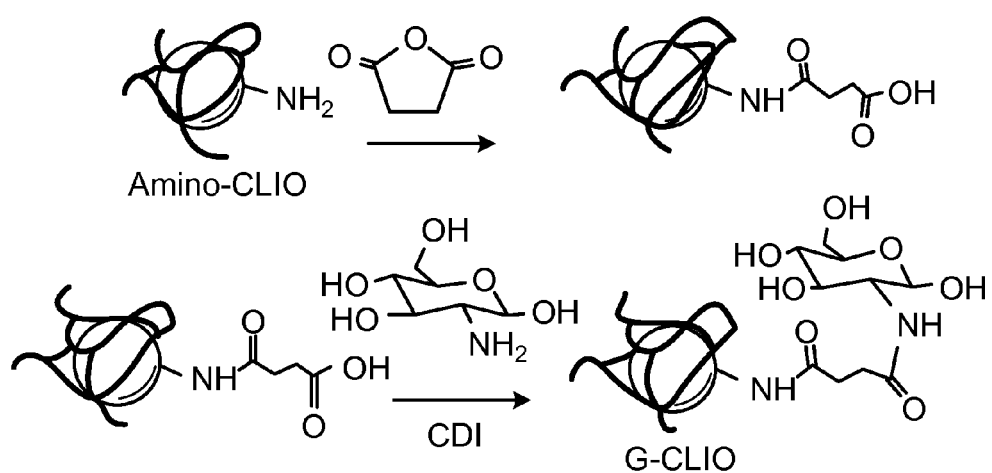
FIG. 2 is a reaction scheme showing the synthesis of glucose linked cross-linked iron oxide nanoparticle (Glu-CLIO).

Nanoparticles 20 having a moiety corresponding to formula (I) can be prepared by contacting amino-CLIO ($NH_2$-CLIO) with succinic anhydride (pH 8.5) followed by 2-aminoglucose in the presence of a carbodiimide (e.g. a water soluble carbodiimide, e.g., 1-ethyl-3-(3-dimethylaminopropyl) carbodiimide hydrochloride (EDC)/N-hydroxysuccinimide (NHS), pH 6.0 (see FIG. 2). Such nanoparticles are referred to herein as "G-CLIO," "Glu-CLIO," or "Glu-CLIO nanoswitches."

Folic acid (FA) can be conjugated to $NH_2$-CLIO using a water soluble carbodiimide (e.g. EDC/NHS, pH 6.0) to provide nanoparticles 20 having a folic acid-containing moiety linked to the nanoparticle. Such nanoparticles are referred to herein as "FA-CLIO" or "FA-CLIO nanoswitches."

Influenza hemagglutinin peptide (HA) can be conjugated to $NH_2$-CLIO with, e.g., N-succinimidyl 3-(2-pyridyldithio) propionate (SPDP) (PBS buffer, pH 7.4 to provide nanoparticles 20 having an HA-containing moiety linked to the nanoparticle. Such nanoparticles are referred to herein as "HA-CLIO" or "HA-CLIO nanoswitches."

The nanoparticles used in the sensors described herein can also be prepared using the conjugation chemistry described in, e.g., Sun, E. Y., Josephson, L., Kelly, K., Weissleder, R. *Bioconjugate Chemistry* 2006, 17, 109-113, which is incorporated by reference herein. The nanoparticles used in the sensors described herein can also be prepared using "click chemistry" methodology described in, e.g., Kolb et al, *Angew Chem Int Ed Engl.,* 2001, 40:2004-2021.

The combination of nanoparticles 20, analyte, and protein binding agent 18 used in the sensors described herein can be selected as desired.

In some embodiments, the combination of nanoparticles, analyte, and binding agent used in the sensors can be based on the assay configurations described in, e.g., Josephson, et al., *Angewandte Chemie, International Edition* 40, 3204-3206 (2001); Perez et al., *Nat Biotechnol* 20, 816-20 (2002); J. M. Perez et al. *J Am Chem Soc* 124, 2856-7 (2002); and Tsourkas et al. *Angew Chem Int Ed Engl* 43, 2395-9 (2004) (a water relaxation assay using antibodies and surface functionalized nanoparticles detecting enantiomeric impurities indicating the ability of the MR-based assay to measure the levels of drugs or metabolites rather than glucose), each of which is incorporated by reference herein.

By way of example, Table 2 illustrates representative assay configurations.

TABLE 2

| Relaxation Sensor Assay Type or Configuration | Exogenous Analyte | Binding Agent | Example and Comment |
|---|---|---|---|
| See, e.g., FIG. 1A | glucose | conA | See Examples |
| See, e.g., FIG. 1A | Chiral Moieties (e.g., Small molecule Enantiomers) | Monoclonal antibodies | See, e.g., All Figures of Tsourkas, A., Hofstetter, O., Hofstetter, H., Weissleder, R., and Josephson, L. (2004). Magnetic relaxation switch immunosensors detect enantiomeric impurities. Angew Chem Int Ed Engl 43, 2395-2399. |
| See, e.g., FIG. 1A | Monovalent analytes (e.g., therapeutic agents, peptides, nucleic acids, etc.) | Multivalent binding agent (e.g., able to bind two or more nanoparticles simultaneously; e.g., Lectin, polyclonal or monoclonal antibody) | Multivalent Functionalized nanoparticle must be (able to two binding proteins simultaneously) |
| See, e.g., FIG. 1B | Nucleic acid | oligonucleotide | See e.g., all figures of Josephson, L., Perez, J. M., and Weissleder, R. (2001). Magnetic nanosensors for the detection of oligonucleotide sequences. Angewandte Chemie, International Edition 40, 3204-3206. |
| See, e.g., FIG. 1B | mRNA | oligonucleotide | E.g., FIG. 4 of Perez, J. M., Josephson, L., O'Loughlin, T., Hogemann, D., and Weissleder, R. (2002). Magnetic relaxation switches capable of sensing molecular |

TABLE 2-continued

Figure 5A:
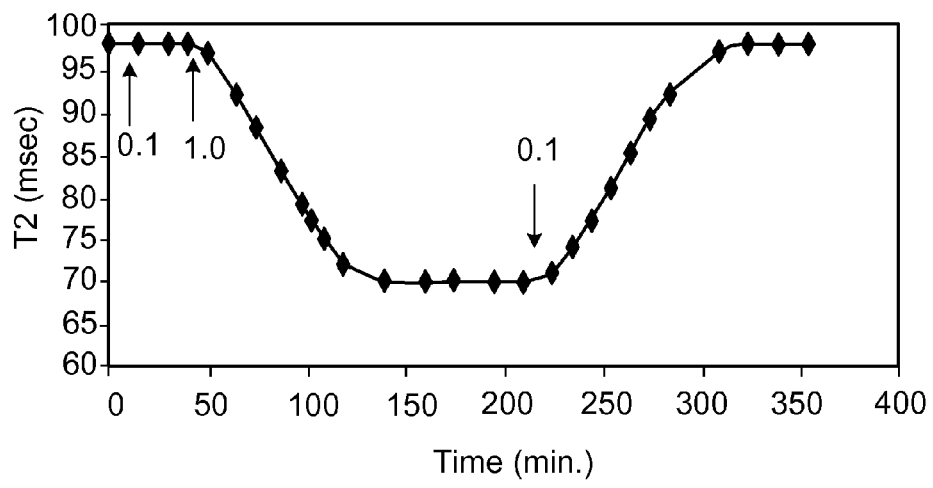
FIG. 5A is a graphical representation of changes in T2 relaxation times obtained by contacting a water relaxation sensor with solutions of varying external glucose concentrations. Sensor was first placed in PBS with 0.1 mg/mL glucose, then in buffer with 1.0 mg/mL glucose and returned to a solution of 0.1 mg/mL glucose. Conditions were essentially the same as described with respect to FIGS. 3A and 3B.
Figure 5A:
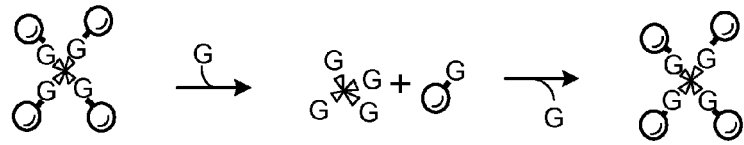

| Relaxation Sensor Assay Type or Configuration | Exogenous Analyte | Binding Agent | Example and Comment |
| --- | --- | --- | --- |
| See, e.g., FIG. 1B | GFP | Polyclonal antibodies | interactions. Nat Biotechnol 20, 816-820 E.g., FIG. 5A, Perez, J. M., Josephson, L., O'Loughlin, T., Hogemann, D., and Weissleder, R. (2002). Magnetic relaxation switches capable of sensing molecular interactions. Nat Biotechnol 20, 816-820. |
| See, e.g., FIG. 1B | Proteins, polysaccharide | Proteins, | Multivalent Exogenous Analyte (able to simultaneously bind two or more nanoparticles). Multivalent functionalized nanoparticle (able to bind to two or more analytes simultaneously.) |

In some embodiments, the sensors described herein can be used to monitor physiological concentrations of glucose (see Examples section).

In general, any MR-based method that is capable of discriminating water T2 relaxation times in the sensor chamber from those outside of the sensor chamber can be used to monitor the sensors. Such methods can be MR imaging or MR non-imaging methods.

For example, in applications where a single water relaxation sensor is employed, and the T2 of non-sensor, bulk water is uniform, determining the relaxation properties of sensor water may not necessarily require an MR imager or a two-dimensional matrix of water relaxation data. Any non-imaging method capable of distinguishing the properties of the MR signal emanating from inside the sensor from those of the bulk water could be used. Thus, far simpler and less costly types of instrumentation than a clinical MRI instrument can distinguish the relaxation properties sensor water from bulk water. First, the sensor can be implanted in a tube of flowing tube of fluid, minimizing the volume of a homogeneous magnetic field needed but still using the spatial encoding methods of MRI instrumentation. Second, the applied magnetic field need not be homogeneous, a requirement of magnets used to generate MR images. Selective excitation magnets were considered in early MR imager designs (see, e.g., Z. Abe, K. Tanaka, Y. Yamada, Radiat Med 2, 1-23). A variable field strength hand-held magnet and excitation/receiver coil are used for analyzing the relaxation properties of samples within several millimeters of the magnet in commercial devices, see, e.g., on the Internet, minispec.com/products/ProFiler.htm These devices can be used with the new sensors.

Solvent, (e.g., water), spin-spin relaxation times (T2) can be determined by relaxation measurements using a nuclear magnetic resonance benchtop relaxometer. In general, T2 relaxation time measurements can be carried out at 0.47 T and 40° C. (Bruker NMR Minispec, Billerica, Mass.) using solutions with a total iron content of 10 μg Fe/mL.

Alternatively, T2 relaxation times can be determined by magnetic resonance imaging of 384-well plates (50 μL sample volume), allowing parallel measurements at higher throughput. In general, magnetic resonance imaging can be carried out using a 1.5 T superconducting magnet (Sigma 5.0; GE medical Systems, Milwaukee, Wis.) using T2-weighted spin echo sequences with variable echo times (TE=25-1000 ms) and repetition times (TR) of 3,000 ms to cover the spectrum of the anticipated T2 values. This technique is described in, for example, Perez, J. M., et al. Nat Biotechnol 2002, 20, 816-820; and Hogemann, D., et al. Bioconjug Chem 2002, 13, 116-121.

While not wishing to be bound by theory, it is believed that nanoparticle aggregation is associated with an increase in R2 relaxivity of nanoparticles, but not necessarily with R1 relaxivity. See, e.g., Table 1 Josephson, L., Perez, J. M., and Weissleder, R. (2001). "Magnetic nanosensors for the detection of oligonucleotide sequences." *Angewandte Chemie International Edition* :3204-3206. Relaxivity, R=change in relaxation rate (1/T) per change in concentration by 1 mM. Since there is essentially no change or relatively little change in R1 associated with nanoparticle aggregation, the measurement of T1 can be used to determine nanoparticle concentration, while measurements of T2 can be used to determine nanoparticle aggregation. This method can use by way of example equations (1)-(3) below, where NP=nanoparticle, and $T1_o$ and $T2_o$ are the relaxation times of sensor water in the absence of nanoparticles. [A], the concentration of analyte, can be a simple or complex function of R2, which reflects the aggregation state of the particles.

$$[NP] = (1/T1_o - 1/T1_{NP})/R1 \quad (1)$$

$$(1/T2_o - 1/T2_{NP})/[NP] = R2 \quad (2)$$

$$[A] = kR2 \text{ or } [A] = f(R2) \quad (3)$$

Nanoparticle aggregation can also be determined without measurement of T2 as the examples below indicate.

1. Measurement of the T2*, or free induction decay, rather than T2.

2. Measurement of amount of relaxation properties of specific class of water protons in the sample using an off resonance radiation, that is radiation that is not precisely at the Larmour precession frequency. In this measure a frequency of incident radiation not precisely at the Larmour precession frequency is employed.

3. Measurement of the height of a single echo obtained with a T2 measuring pulse sequence rather than a complete echo train. Normal T2 measurements utilize the declining height of a number of echoes to determine T2.

4. Shifting the frequency or strength of the applied magnetic field, measuring the broadness of the proton absorption peak. Broader the peaks or energy absorption are correlated with higher values of T2.

In some embodiments, with instrumentation designed solely for distinguishing the relaxation of sensor water protons from bulk water protons, relaxation based sensors can be used to monitor exogenous analytes in any enclosed, aqueous system including bioreactors or fluids in a variety of industrial applications.

In some embodiments, the sensor can be an implantable sensor implanted subcutaneously (e.g., the sensor can be implanted in an extremity of a subject so as to avoid having the entire body of the subject surrounded by the magnetic field).

EXAMPLES

The invention is further illustrated by the following Examples. The Examples are provided for illustrative purposes only, and are not to be construed as limiting the scope or content of the invention in any way.

General

Synthesis of surface functionalized nanoparticles: EDC (1-ethyl-3-(3-dimethylaminopropyl)carbodiimide hydrochloride), sulfo-NHS (sulfosuccinimidyl ester of N-hydroxysuccinimide) were purchased from Pierce. SPDP (N-succinimidyl 3-(2-pyridyldithio)propionate) was purchased from Molecular Biosciences. All other chemicals were purchased from Sigma Aldrich and used as received. Amino-CLIO nanoparticles were synthesized by crosslinking the dextran coating with epichlorohydrin and reacting it with ammonia, to provide primary amine groups (see, e.g., Josephson, L.; Tung, C. H.; Moore, A.; Weissleder, R. *Bioconjug Chem.* 1999, 10, (2), 186-91.; and Josephson, L.; Perez, J. M.; Weissleder, R. *Angewandte Chemie, International Edition* 2001, 40, (17), 3204-3206). The number of amines were determined by reaction with SPDP and treatment with dithiothreitol that releases pyridine-2-thione (P2T) (see, e.g., Zhao, M.; Kircher, M. F.; Josephson, L.; Weissleder, R. *Bioconjug Chem* 2002, 13, (4), 840-4). Protein binding agents ConA, anti-folate acid antibody (anti-FA) and anti-HA antibody (anti-HA) were purchased from Sigma.

For T2 measurements, a 0.47 T relaxometer (Bruker) was used. Measurements were made in 0.5 mL of PBS at 40° C. The concentration of surface functionalized nanoparticles was between 8 and 15 µg/ml Fe, adjusted to give a starting T2 of about 150 msec. The concentrations of binding proteins were 1 mg/mL (ConA), 0.1 mg/mL (anti-HA) and 0.1 mg/mL (anti-FA). After addition of each amount of analyte, T2 was recorded several times until it reached a stable value.

The size of nanoparticles was measured by a laser light scattering (Zetasizer, Malvern Instruments) in 1 mL PBS at 23° C. and is the volume-based size. The concentration of surface functionalized nanoparticles was between 25 and 35 µg/ml Fe, which is believed to be optimal for obtaining nanoswitch size distribution on this instrument. The concentrations of binding proteins were 1 mg/mL (Con A), 0.5 mg/mL (anti-HA) and 0.5 mg/mL (anti-FA). Repeated size measurements were made at 40-80 minutes post addition of binding protein or analyte and were essentially constant over than period. Results shown are typical size distributions. For reversion to the dispersed states (FIGS. 4E, 8E and 9E), 600 mg/dl glucose, 500 nM HA and 30 nM FA were employed.

For some of the experiments enclosing the nanoswitches in a semipermeable device, 0.25 ml of Glu-CLIO (10 µg/mL Fe) and ConA (1 mg/mL) were placed in membrane with a 10 kDa cutoff (Spectra/Por, Fischer). The device was transferred back and forth between solutions with glucose concentrations of 20 mg/dl and 200 mg/dl. It was removed at different times and placed in a NMR tube. T2 values were obtained in less than 30 seconds and the device placed in the original glucose solution of a glucose solution with a different concentration.

Data processing: The line drawn for cyclical changes in T2 was obtained by use of the following equation: T2=A*sin (B*time+C)+Y, A=15.58, B=0.0253836, C=50.283 and Y=83.8099.

Example 1

Glu-CLIO Nanoswitches

Summary

To demonstrate the water relaxation sensor we designed a prototype for monitoring physiological concentrations of glucose. We employed conconavalin A as a binding protein and synthesized a glucose functionalized magnetic nanoparticle (Glu-CLIO). Conconavalin A (ConA) is a tetravalent lectin that is known to react with glucose. Some of the sensors were prepared having a walled enclosure with a pore size of 3 kDa. In general, the walled enclosure of the sensors retained the Glu-CLIO nanoparticle and ConA, while permitting glucose to freely enter or leave the sensor.

Example 1A

Preparation of Glu-CLIO

MION-47 and amino-CLIO (25-35 nm) were prepared as described elsewhere. D-Glucose, D-(+)-Glucosamine hydrochloride, succinic anhydride, Concanavalin A (ConA) and Sephadex G-25 were from Sigma Aldrich Co. 1-Ethyl-3-(3-dimethylaminopropyl)carbodiimide hydrochloride (EDC) and sulfo-N-hydroxysuccinimide (sulfo-NHS) were from Pierce (Rockford, Ill.). To synthesize a glucose-functionalized nanoparticle (Glu-CLIO), $NH_2$-CLIO was first converted to a carboxylic group functionalized nanoparticle, followed by coupling of 2-amino-glucose using a water-soluble carbodiimide. To obtain a carboxylic functionalized CLIO, 2.0 mg succinic anhydride was added into 200 uL $NH_2$-CLIO (10 mg Fe/mL, 42 $NH_2$ per 2064 Fe) with 300 uL (0.1 M) $NaHCO_3$ buffer, pH 8.5. The mixture was incubated at room temperature for two hours and succinic acid removed using a Sephadex G-25 column eluted with MES buffer (0.5 M NaCl, 0.05 M MES), pH 6.0. To conjugate 2-amino-glucose to carboxy functionalized CLIO (CLIO-COOH), 2 mg EDC and 2 mg sulfo-NHS were added into 500 uL CLIO-COOH (mg Fe/mL) in MES buffer, pH 6.0. The mixture was allowed to react for two hours at room temperature and purified by Sephadex G-25 column eluted with PBS buffer at pH 7.4. Subsequently 2 mg Glucosamine was added into above solution and the mixture reacted for one hour at room temperature. Unreacted glucosamine was removed with Sephadex G-25 in PBS.

Example 1B

Glu-CLIO-ConA-Glucose Tube Assay

Relaxation times were obtained at 0.47 T, 40° C. using a Minispec relaxometer (Bruker).

To demonstrate the interaction between Glu-CLIO, ConA and glucose, experiments were performed directly in NMR tube (no semi-permeable walled enclosure), 10 ug Fe/mL, 800 ug/mL ConA. All experiments were performed in PBS with 1 mM $CaCl_2$ and 1 mM $MgCl_2$. Transverse relaxation times (T2' s) were measured in the relaxometer, Bruker Minispec® NMS 120 at 0.47 T and 40° C. Size was determined with a Zetasizer HS 1000® (Malvern Instruments, Marlboro, Mass.) in the buffer above with Glu-CLIO at 20 ug Fe/mL, followed by the addition of ConA to 1 mg/mL and 1.5 mg/mL glucose. All experiments used these concentration of ions, buffer, ConA and Glu-CLIO.

Figure 3A:
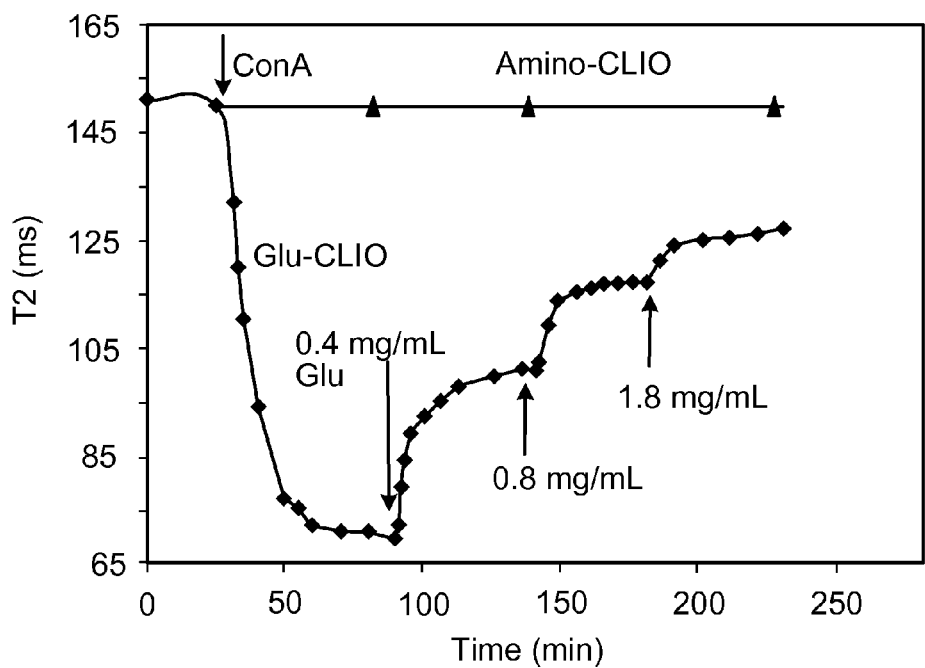
FIG. 3A is a graphical representation of changes in T2 relaxation times obtained in a tube based water relaxation assay for glucose using the Glu-CLIO/ConA configuration. Amino-CLIO does not react with ConA binding protein, as indicated by a stable T2 relaxation time after ConA addition. Attachment of 2-amino-glucose (G) results in a functionalized nanoparticle, Glu-CLIO, which shows a T2 drop upon addition of a glucose-binding protein (ConA). The T2 drop is reversed by the addition of glucose. The data is indicative of nanoparticle aggregation and disaggregation. For T2 measurements, 0.5 mL of Glu-CLIO (10 ug Fe/mL), 800 ug/mL ConA in PBS with 1 mM $CaCl_2$ and 1 mM $MgCl_2$ were used.
Figure 3A:
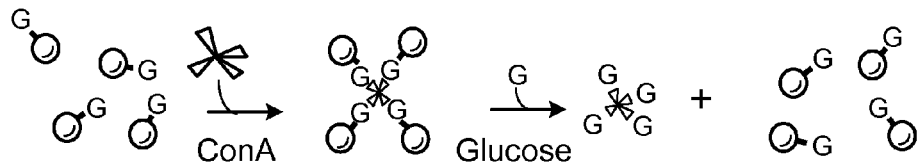
Figure 3B:
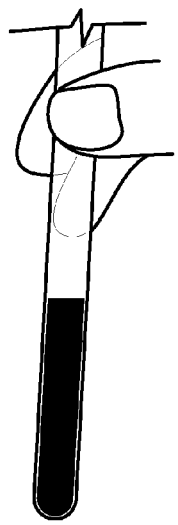
FIG. 3B is a photograph of the assay apparatus. Iron concentration in the photograph was increased to 100 ug Fe/mL for better contrast.

As shown in FIG. 3A, the addition of ConA to Glu-CLIO resulted in a drop in T2 that reached a plateau after about 50 minutes, while no change was obtained with amino-CLIO. Associated with the ConA induced T2 change was an increase in the size of the Glu-CLIO nanoparticle from 30 nm to 301 nm by laser light scattering, indicating nanoparticle clustering was associated with ConA addition and the T2 increase, and that the system was behaving like a magnetic relaxation switch. Addition of glucose then caused a partial reversibility of the T2 drop, with T2 values again reaching a plateau after about 100 minutes, 150 minutes, and 200 minutes. This type of response was seen with additions that produced concentrations of 0.4, 0.8 and 1.8 mg/mL glucose. The sensor responded to 0.2 to 1.8 mg/mL glucose, which is approximately the physiological range of plasma glucose in humans. The apparatus is shown in FIG. 3B.

Example 1C

Glu-CLIO-ConA-Glucose Tube Assay

Glu-CLIO nanoswitches were diluted into tubes to obtain a T2 of 153 msec. Upon addition of ConA, T2 decreased and reached a plateau value of 65 msec (see FIG. 4A).

Figure 4A:
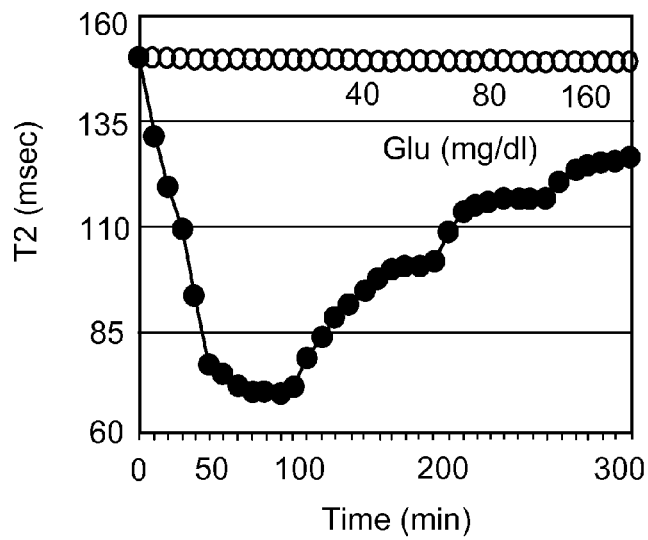
FIG. 4A is a graphical representation of changes in T2 relaxation times obtained in a tube based assay for glucose using the Glu-CLIO nanoswitch/ConA configuration. Addition of ConA to Glu-CLIO caused a initial T2 drop, which was reversed by the addition of increasing concentrations of glucose.
Figure 4B:
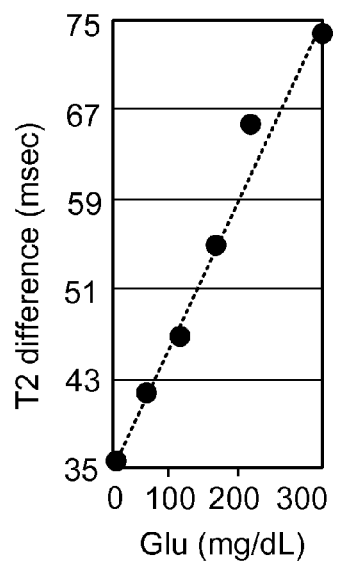
FIG. 4B is a graphical representation of changes in T2 values (at the plateau) obtained with different glucose concentrations.

Addition of increasing concentrations of glucose reversed this effect, with a constant T2 value observed at each glucose concentration (see FIG. 4B). The change in plateau T2 values occurred in a linear fashion over the physiological range of glucose concentrations (see FIG. 4B).

Figure 4E:
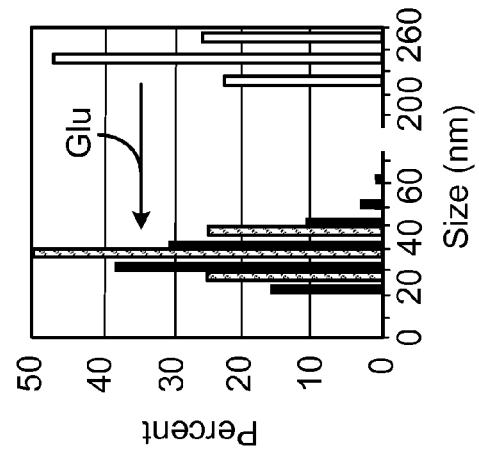
FIGS. 4C, 4D, and 4E are graphical representations of particle size distribution as obtained by light scattering experiments.
Figure 4D:
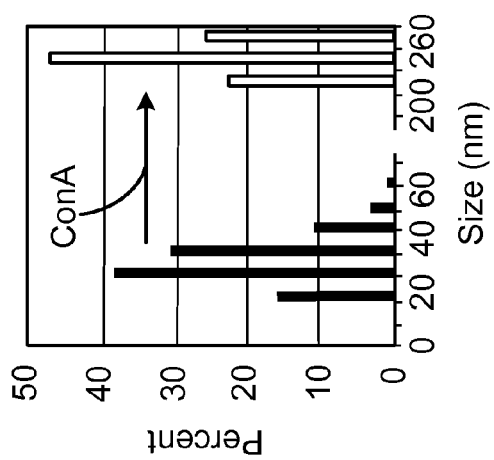
Figure 4C:
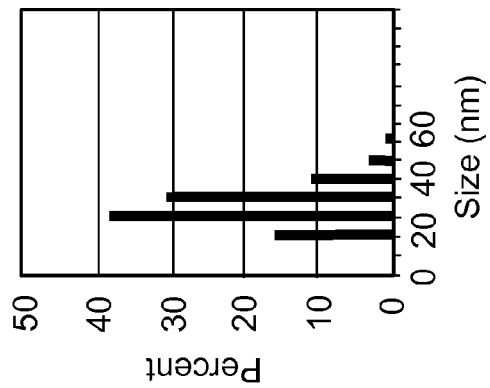

To further investigate the interconversion (switch) between the initial dispersed nanoparticle state and the microaggregated state, light scattering measurements were obtained (see FIGS. 4C, 4D, and 4E). Dispersed nanoswitches had a mean diameter of 26 nm (see FIG. 4C), which increased to a mean diameter of 230 nm upon addition of ConA (see FIG. 4D), and which returned to its original size distribution with the addition of glucose (400 mg/dl) (see FIG. 4E). The initial T2 value of 153 msec (see FIG. 4A) was not achieved upon addition of the glucose. The discrepancy between the initial and final T2 value is believed to be due to a slight dilution of iron that accompanied the addition of concentrated solutions of glucose. Based on the return of nanoswitches to their original size distribution (see FIG. 4E), a complete interconversion between dispersed and microaggregated nanoswitch states was achieved by glucose addition.

Example 1D

Glu-CLIO-ConA-Glucose Sensor Assay

Figure 5B:
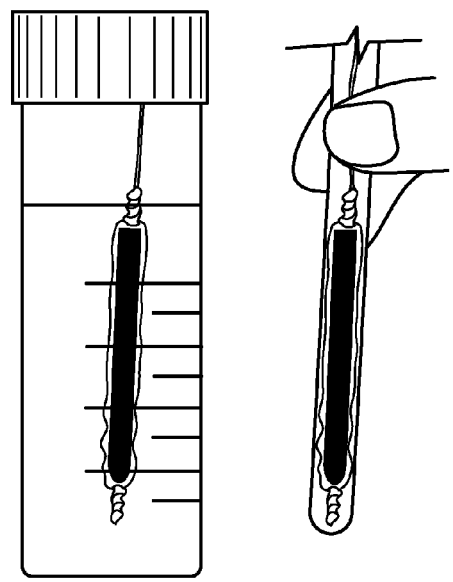
FIG. 5B is a photograph of the sensor and the apparatus for containing the glucose-containing sample media.

We next placed the components of the tube-based relaxation assay (ConA and Glu-CLIO as used in FIGS. 3A and 3B) in the semi-permeable device shown in FIG. 5B, to obtain a water relaxation based sensor (volume ~0.5 mL, 3 kDa pores). We allowed the sensor to equilibrate with 0.1 mg/mL glucose overnight and obtained a stable T2 of 98 msec (see FIG. 5A), obtained by placing it in a glass tube used with the MR relaxometer. The sensor was then placed in a second tube (1 mg/mL glucose) and T2 values monitored (see FIG. 5A). A new plateau of 70 msec was attached after about 100 minutes, indicating glucose-induced dispersion of the Glu-CLIO nanoparticles (see FIG. 5A). The sensor was then placed in a third tube with 0.1 mg/mL glucose. T2 increased and returned to a plateau of T2 again at 98 msec (see FIG. 5A). Thus, the water relaxation based glucose sensor uses a T2 dependent equilibrium between ConA and Glu-CLIO to sense external glucose in a reversible fashion.

Similar results were obtained when Glu-CLIO and ConA were enclosed in a semi-permeable sensor to interact with glucose in the external sensor environment (FIG. 5B), using 500 uL of G-ConA and ConA as above were placed in a membrane of cellulose ester with a 1 kDa cutoff and diameter of 7.5 mm (Spectra/Por®, Fisher Scientific). The sensor was placed in 50 mL tube with a magnetic stir at the bottom of tube for mixing. At various times the external concentration of glucose was varied, and the sensor removed, placed in an NMR tube, and T2 determined as above (results not shown).

Example 1E

Glu-CLIO-ConA-Glucose Sensor Assay with MRI Imaging

Figures 6A, 6B, 6C:
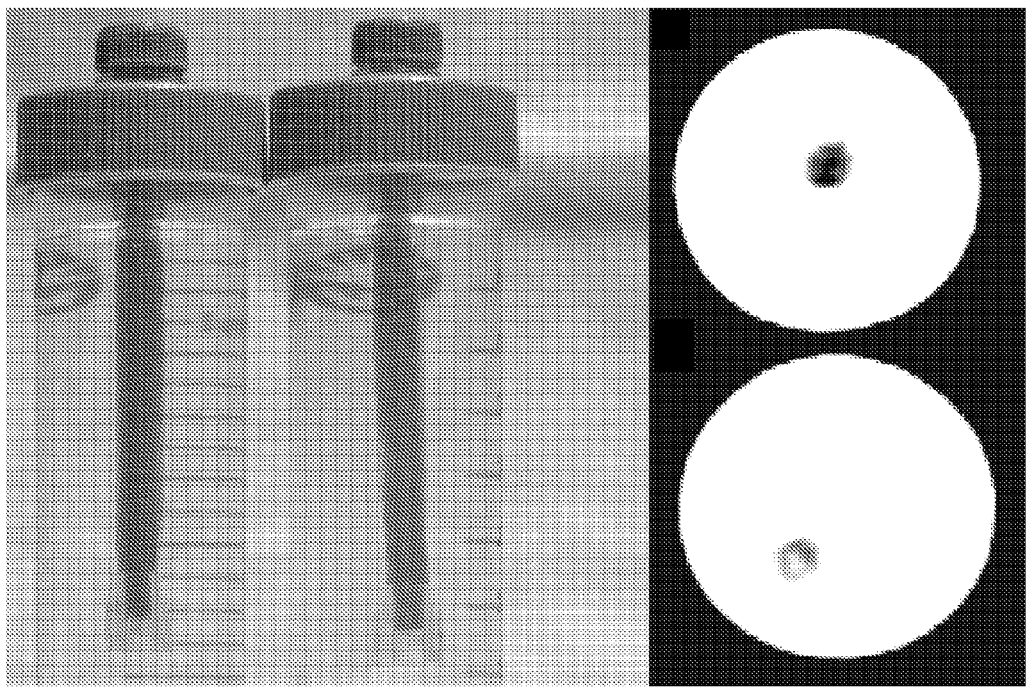
FIGS. 6A, 6B, and 6C are images corresponding to the reaction of a water relaxation sensor to glucose visualized by MRI.

We placed Glu-CLIO-ConA sensors in two test tubes, one with 2 mg/mL glucose and without glucose and imaged the tubes using a clinical MR imager (see FIG. 6A). To demonstrate the ability of MRI to detect the interaction between Glu-CLIO and ConA the semi-permeable membrane, Glu-CLIO (10 ug Fe/mL) and Con A (800 ug/mL) were placed in a 1 kDa cutoff, 5 mm diameter semi-permeable tube (Spectra/Por Irradiated Dispodialyzer, Fisher) and the sensor placed in a 50 mL tube as above. After 2 hours, the stir bar was removed and images obtained on a clinical GE Signa 1.5 T unit. (Image size 256×192, field of view 7×14 Cm, slice thickness 1.5 mm using a turbo spin echo pulse sequence, TR 2500, TE65).

As shown in FIGS. 6B and 6C, the sensor in the high glucose environment had higher signal intensity (brighter image), reflecting nanoparticle dissociation and a higher (longer) T2. Thus, the concentration of external glucose altered the signal intensity of water within the sensor that was evident on an MR image.

Example 1F

Glu-CLIO-ConA-Glucose Sensor Assay with MRI Imaging

Figure 7:
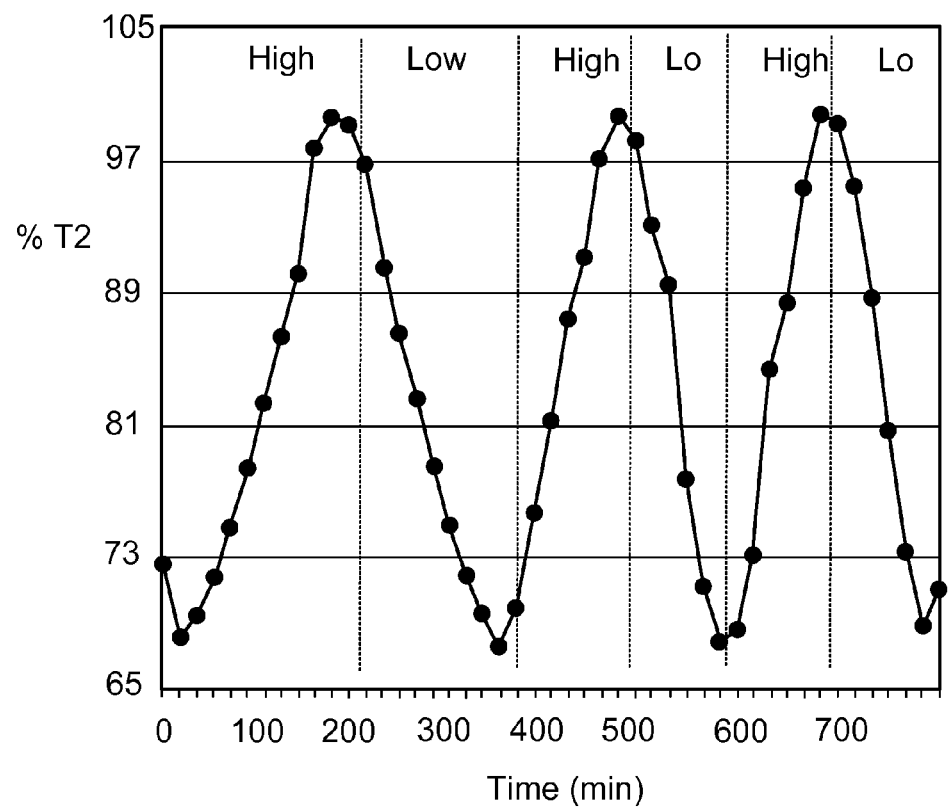
FIG. 7 is a graphical representation of time dependent changes in T2 with increasing and decreasing glucose concentrations. The Glu-CLIO nanoswitch/ConA system used in the experiments described in FIGS. 4A-4E was placed in a semipermeable device so that glucose could be cycled between low and high concentrations, causing nanoparticles in the sensor to shift back and forth between a low T2 state and high T2 state.

We further examined whether the nanoswitch/binding protein equilibrium would be maintained if the nanoswitches and binding proteins were enclosed in a semipermeable device, with pores that would allow analyte to enter but which would retain nanoparticles and binding protein. This would allow analyte concentrations to be raised or lowered, depending on the sensor environment (dialysate). A number of different units were investigated as possible including Spectra/Por tubing, Slide-A-Lyzer microcassettes and dialysis fibers. Spectra/Por tubing permitted the rapid and repeated transfer of the sensor from a 100 mL beaker, where glucose concentrations were cycled between 20 mg/dl and 400 mg/dl to an MR relaxometer, where T2 measurements were made in less than a minute. The T2 of sensor water changed in cycled between about 68 and 100 msec as it responded to changing concentrations of glucose (see FIG. 7). Both increases and decreases in glucose concentration resulted in alteration of the nanoswitch microaggregation state, evident by changes in T2, further demonstrating the equilibrium nature of nanoswitches.

Example 2

HA-CLIO Nanoswitches

Example 2A

Preparation of HA-CLIO

To synthesize hemagglutinin peptide-CLIO, a thiolated influenza hemagglutinin (HA) peptide with a C-terminal cysteine (YPYDVPDVAGGC) was synthesized by using Fmoc chemistry on Rink amide resin (Calbiochem, NovaBiochem) and was purified by reverse phase HPLC. The molecular weight of HA was confirmed by MALDI-TOF. To attach HA to nanoparticle, amino-CLIO was first reacted with SPDP. After purification, 200 µL SPDP modified CLIO (5.0 mg/mL Fe) in PBS buffer, pH 7.4 was mixed with 100 µL of HA (50 mM) in DMSO. Reaction proceeded for 2 hours at room temperature. The CLIO conjugate was separated by Sephadex G-25 column and eluted with PBS buffer, pH 7.4. The number of peptides per nanoparticle was determined by the SPDP method. Nanoparticles had 25 HA per 2000 Fe and the size distribution shown in FIG. 3.

Example 2B

HA-CLIO-anti-HA-HA Tube Assay

Relaxation times were obtained at 0.47 T, 40° C. using a Minispec relaxometer (Bruker).

Figure 8A:
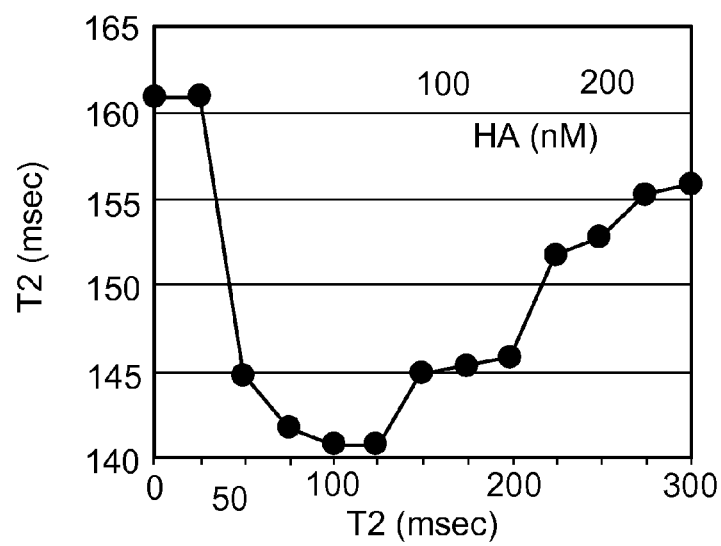
FIG. 8A is a graphical representation of changes in T2 relaxation times obtained in a tube based assay for influenza hemagglutinin peptide (HA) using the HA-CLIO nanoswitch/antibody to HA (anti-HA) configuration. Addition of anti-HA to HA-CLIO caused an initial T2 drop, which was reversed by the addition of increasing concentrations of HA.
Figure 8B:
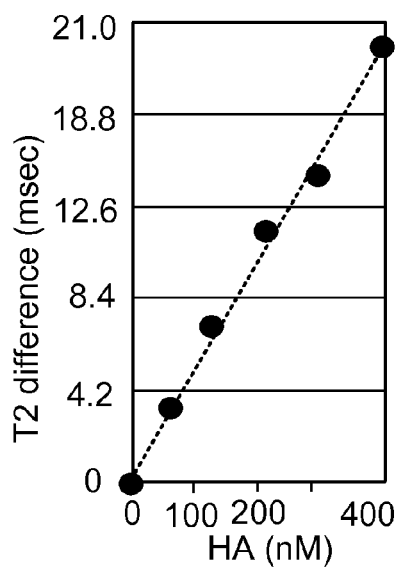
FIG. 8B is a graphical representation of changes in T2 values obtained with different HA concentrations.
Figure 8E:
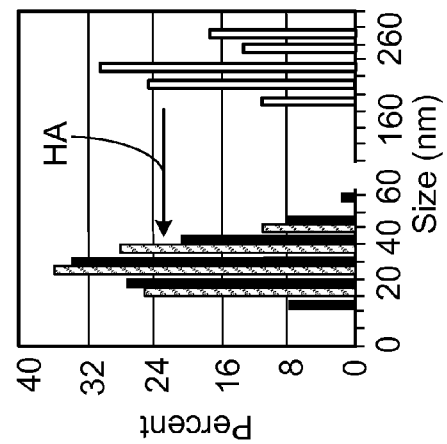
FIGS. 8C, 8D, and 8E are graphical representations of particle size distribution as obtained by light scattering experiments.
Figure 8D:
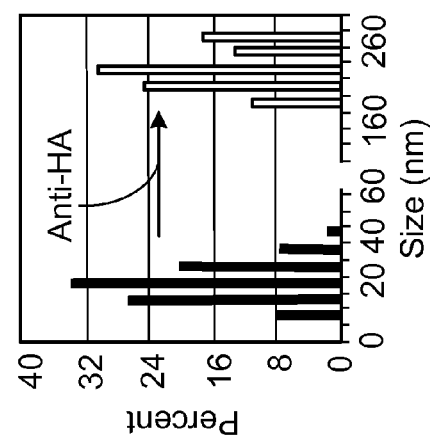
Figure 8C:
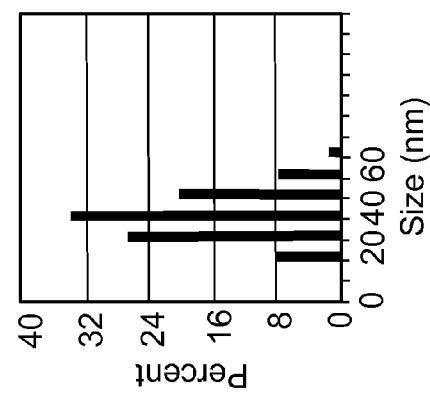

Nanoswitches had similar properties when HA-CLIO replaced Glu-CLIO and antibody to HA (anti-HA) replaced ConA as shown in FIGS. 8A-8E. As shown in FIG. 8A, T2 dropped from 162 to 141 msec with the addition of anti-HA. Plateau values of T2 changed over a range of HA concentrations between 50 and 400 nM (FIG. 8B), which was about 80 fold lower than the concentrations of glucose needed to change T2 (2.5 µM-20 µM, FIG. 4B). Again light scattering data indicated that the analyte (HA) was capable of essentially completely reversing microaggregate formation (see FIGS. 8C, 8D, and 8E).

Example 3

FA-CLIO Nanoswitches

Example 3A

Preparation of FA-CLIO

To synthesize FA-CLIO, amino-CLIO in PBS buffer, pH 7.4 was first exchanged with MES buffer (50 mM MES hydrate, 0.1 M NaCl), pH 6.0 and the solution was concentrated to 5.0 mg/mL Then 100 µL (50 mM) folic acid in DMSO was added to 200 µL amino-CLIO (5.0 mg/mL Fe) in MES solution, pH 6.0. This was followed by the addition of excess EDC (0.96 mg, 5 µmol) and sulfo-NHS (1.1 mg, 5 µmol) in 100 µL DMSO. Reaction proceeded at room temperature for 2 hours and the product was purified by Sephadex G-25 column and eluted with PBS buffer, pH 7.4. Attachment of FA was quantified by the loss of amine groups using SPDP, see above, and was 33 FA per 2000 Fe with the size distribution shown in FIG. 9C.

Example 3B

FA-CLIO-anti-FA-FA Tube Assay

Relaxation times were obtained at 0.47 T, 40° C. using a Minispec relaxometer (Bruker).

Figure 9A:
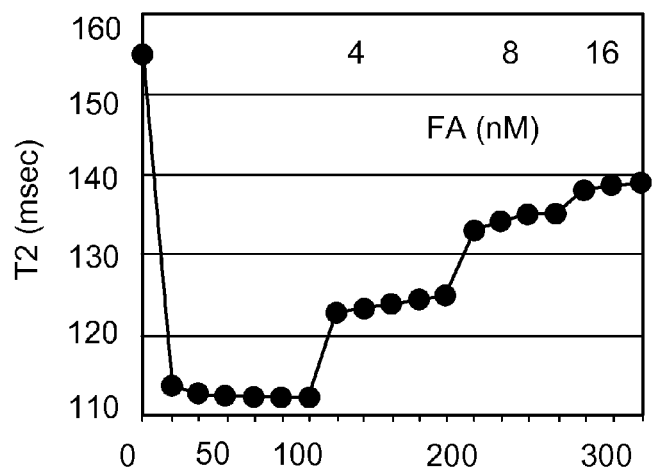
FIG. 9A is a graphical representation of changes in T2 relaxation times obtained in a tube based assay for folic acid (FA) using the FA-CLIO nanoswitch/antibody to FA (anti-FA) configuration. Addition of anti-FA to FA-CLIO caused a initial T2 drop, which was reversed by the addition of increasing concentrations of FA.
Figure 9B:
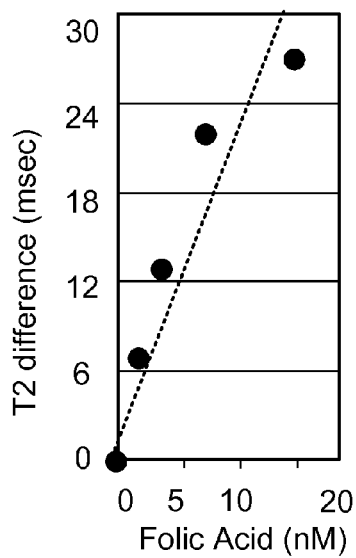
FIG. 9B is a graphical representation of changes in T2 values obtained with different FA concentrations.
Figure 9E:
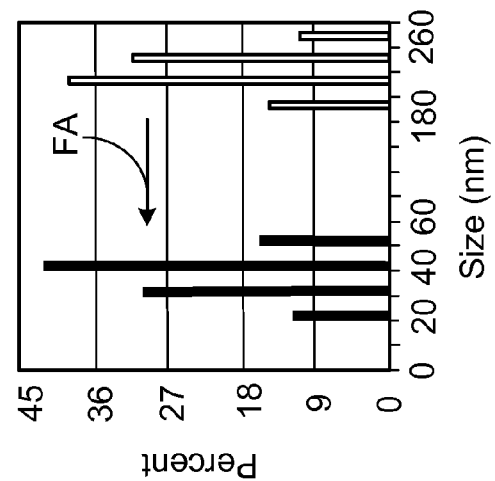
FIGS. 9C, 9D, and 9E are graphical representations of particle size distribution as obtained by light scattering experiments.
Figure 9D:
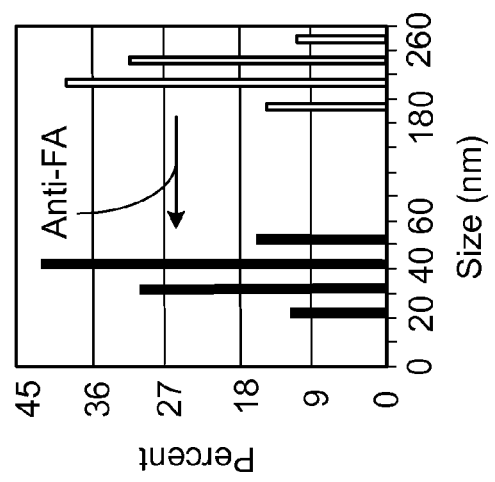
Figure 9C:
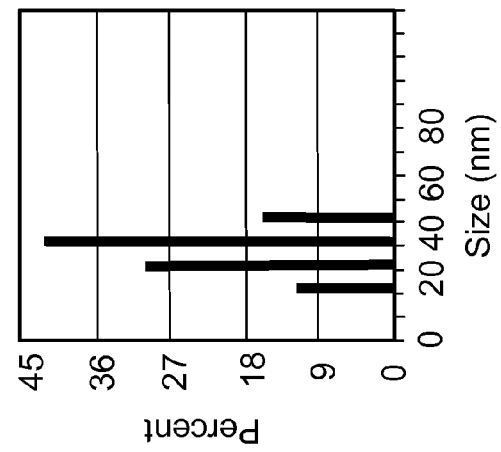

The properties of the nanoswitch system were examined with FA-CLIO nanoparticles and anti-FA as the binding protein. As shown in FIG. 9A, T2 dropped from 155 msec to 113 msec with anti-FA addition. The range or concentrations of FA associated with changing T2 values are shown in FIG. 9B (5-20 nM) and was about 1000 fold lower than the concentrations of glucose measured (2.5 µM-20 µM, FIG. 4B). Again, light scattering data indicated that the analyte (HA) was capable of essentially completely reversing microaggregate formation (see FIGS. 9C, 9D, and 9E).

We conclude that surface functionalized nanoparticles and binding proteins maintained an equilibrium, continuously switching between a dispersed (disaggregated), low T2 state (20-40 nm) and microaggregated high T2 state (200-250 nm), depending the concentration of exogenous analyte. Based on light scattering data, high concentrations of exogenous analytes completely reversed microaggregate formation, returning the system to its original dispersed state expected for an equilibrium process. As indicated by the use of nanoswitches and binding proteins for glucose, FA, and HA, nanoswitches were able to detect chemically diverse analytes over a relatively wide range of concentration.

Other Embodiments

A number of embodiments of the invention have been described. Nevertheless, it will be understood that various modifications may be made without departing from the spirit and scope of the invention. For example, two or more chelating moieties can be incorporated into a single monomeric substrate molecule. Accordingly, other embodiments are within the scope of the following claims.

What is claimed is:

1. A method of detecting an analyte in an aqueous sample for periodic or continuous remote monitoring of an analyte concentration in a subject, the method comprising:
   (i) providing a water relaxation sensor comprising:
     (a) a walled enclosure enveloping a chamber, wherein the wall comprises an opening for passage of the analyte into and out of the chamber;
     (b) a plurality of superparamagnetic nanoparticles located within the chamber, each superparamagnetic nanoparticle having at least one moiety that is covalently or noncovalently linked to the nanoparticle; and optionally,
     (c) at least one binding agent located within the chamber; wherein the opening is smaller in size than the nanoparticles, and is larger in size than the analyte; and wherein the moiety and the analyte each bind reversibly to the binding agent, when present, or the analyte binds reversibly to the moiety, to cause a reversible aggregation or disaggregation of the nanoparticles within the chamber in an equilibrium controlled process, wherein the equilibrium is dependent upon, and changes with, analyte concentration;

(ii) implanting the sensor into a subject subcutaneously; and (iii) following step (ii), measuring the spin-spin (T2) relaxation time of a fluid within the chamber, wherein the spin-spin (T2) relaxation time measurement indicates the analyte concentration.

2. The method of claim 1, wherein the wall comprises one or more openings for passage of the analyte into and out of the chamber, wherein each of the openings is smaller in size than the nanoparticles and the binding agent, and each of the openings is larger in size than the analyte.

3. The method of claim 1, wherein the moiety comprises a carbohydrate, an antibody, an amino acid, a nucleic acid, an oligonucleotide, a therapeutic agent or a metabolite thereof, a peptide, or a protein.

4. The method of claim 1, wherein the binding agent is absent.

5. The method of claim 4, wherein: (a) when the analyte is absent, the chamber comprises substantially disaggregated nanoparticles; and (b) when the analyte is present, the chamber comprises one or more nanoparticle aggregates, wherein the nanoparticle aggregate comprises nanoparticles bound to the analyte through the moiety.

6. The method of claim 1, wherein the binding agent is present.

7. The method of claim 6, wherein: (a) when the analyte is absent, the chamber comprises a nanoparticle aggregate, wherein the nanoparticle aggregate comprises nanoparticles bound to the binding agent through the moiety; and (b) when the analyte is present, the nanoparticles are displaced from the binding agent by the analyte, and the chamber comprises substantially disaggregated nanoparticles.

8. The method of claim 1, wherein the nanoparticle aggregate has an overall size of at least about 100 nm.

9. The method of claim 1, wherein the change in nanoparticle aggregation between (i) and (ii) alters the proton relaxation of water inside the chamber, but does not substantially alter the proton relaxation of water outside the chamber.

10. The method of claim 1, wherein the change in nanoparticle aggregation between (i) and (ii) produces a measurable change in the T2 relaxation times of water inside the chamber.

11. The method of claim 1, further comprising the following steps:

(iv) following step (iii), measuring a second spin-spin (T2) relaxation time within the chamber; and (v) on the basis of the difference between the T2 relaxation time of step (iii) and the second T2 relaxation time, determining whether the amount of analyte in the sample has changed, wherein a fluctuation in the observed T2 relaxation time within the chamber indicates a fluctuation in the concentration of analyte.

12. The method of claim 1, wherein the T2 relaxation times is measured using a magnetic resonance imaging method.

13. The method of claim 1, further comprising providing a plurality of water relaxation sensors for detection of two or more analytes.

* * * * *